(12) United States Patent
Gokaraju et al.

(10) Patent No.: US 11,801,277 B2
(45) Date of Patent: Oct. 31, 2023

(54) SYNERGISTIC HERBAL COMPOSITIONS FOR THE TREATMENT OF OBESITY AND OVERWEIGHT

(71) Applicant: LAILA NUTRACEUTICALS, Vijayawada (IN)

(72) Inventors: Ganga Raju Gokaraju, Vijaywada (IN); Venkata Kanaka Ranga Raju Gokaraju, Vijayawada (IN); Rama Raju Gokaraju, Vijayawada (IN); Trimurtulu Golakoti, Vijayawada (IN); Kiran Bhupathiraju, Vijayawada (IN); Venkateswarlu Somepalli, Vijayawada (IN); Venkata Krishna Raju Alluri, Vijayawada (IN); Krishanu Sengupta, Vijayawada (IN)

(73) Assignee: Laila Nutraceuticals, Vijayawada (IN)

( * ) Notice: Subject to any disclaimer, the term of this patent is extended or adjusted under 35 U.S.C. 154(b) by 64 days.

(21) Appl. No.: 16/978,905

(22) PCT Filed: Mar. 5, 2019

(86) PCT No.: PCT/IN2019/050187
§ 371 (c)(1),
(2) Date: Sep. 8, 2020

(87) PCT Pub. No.: WO2019/171397
PCT Pub. Date: Sep. 12, 2019

(65) Prior Publication Data
US 2021/0046135 A1    Feb. 18, 2021

(30) Foreign Application Priority Data
Mar. 5, 2018  (IN) .............................. 201841004317

(51) Int. Cl.
| | | |
|---|---|---|
| *A61K 36/185* | (2006.01) | |
| *A23L 29/30* | (2016.01) | |
| *A23L 33/105* | (2016.01) | |
| *A23L 33/125* | (2016.01) | |
| *A23L 33/00* | (2016.01) | |
| *A61P 3/04* | (2006.01) | |
| *A61K 9/00* | (2006.01) | |
| *A61K 9/68* | (2006.01) | |
| *A61K 36/752* | (2006.01) | |
| *A61K 47/36* | (2006.01) | |

(52) U.S. Cl.
CPC ............ *A61K 36/185* (2013.01); *A23L 29/35* (2016.08); *A23L 33/105* (2016.08); *A23L 33/125* (2016.08); *A23L 33/40* (2016.08); *A61K 9/0056* (2013.01); *A61K 9/0058* (2013.01); *A61K 36/752* (2013.01); *A61K 47/36* (2013.01); *A61P 3/04* (2018.01); *A23V 2002/00* (2013.01); *A61K 2236/333* (2013.01)

(58) Field of Classification Search
CPC .. A61K 36/185; A61K 9/0056; A61K 9/0058; A61K 36/752; A61K 47/36; A61K 2236/333; A61K 8/9789; A61K 2800/5922; A23L 29/35; A23L 33/105; A23L 33/125; A23L 33/40; A61P 3/04; A23V 2002/00; A61Q 19/06
See application file for complete search history.

(56) References Cited

U.S. PATENT DOCUMENTS

| | | | |
|---|---|---|---|
| 7,329,419 B2 | 2/2008 | Yatcilla et al. | |
| 8,541,383 B2 * | 9/2013 | Gokaraju | A61P 3/00 514/25 |
| 8,642,094 B2 * | 2/2014 | Shan | A61K 36/718 424/725 |

(Continued)

FOREIGN PATENT DOCUMENTS

| | | | |
|---|---|---|---|
| CN | 106866779 A | | 6/2017 |
| CN | 10686779 | * | 8/2017 |

OTHER PUBLICATIONS

Ashida H. et al. Prevention Mechanisms of Glucose Intolerance and Obesity by Cacao Liquor Procyanidin Extract. Annals of Nutrition and Metabolism 63(Supp 1)1601, ab PO2766. Sep. 2013. (Year: 2013).*

(Continued)

*Primary Examiner* — Aaron J Kosar
(74) *Attorney, Agent, or Firm* — Kramer & Amado, P.C.

(57) ABSTRACT

The invention discloses synergistic herbal composition comprising combination of first ingredient selected from extracts, fractions, phytochemicals and mixtures thereof derived from *Theobroma cacao* and a second ingredient selected from extracts, fractions, phytochemical and mixtures thereof derived from *Citrus aurantifolia* for obtaining at least one health benefit selected from preventing, controlling or treating obesity and/or overweight; improving lean body mass, improving the browning of White Adipose Tissue/improving formation of brown adipose tissue, increasing basal metabolic rate/resting energy expenditure, increasing thermogenesis, improving thyroid function, maintaining healthy body weight, increasing satiety/, supporting weight loss, improving fat loss and maintaining a slim body. The invention further discloses synergistic herbal compositions comprising *Theobroma cacao* and *Citrus aurantifolia* and optionally comprises at least one ingredient selected from pharmaceutically acceptable excipient/diluent/carrier; methods of treatment and use for the prevention and treatment of obesity/overweight or improving lean body mass or resting energy expenditure in a human or animal.

15 Claims, 7 Drawing Sheets

(56) References Cited

U.S. PATENT DOCUMENTS

| | | | | |
|---|---|---|---|---|
| 9,301,987 | B2* | 4/2016 | Gokaraju | A61K 36/67 |
| 10,960,057 | B2* | 3/2021 | Cornblatt | A61K 31/375 |
| 2004/0202677 | A1* | 10/2004 | Hopkins | A61K 31/555 |
| | | | | 424/195.17 |
| 2006/0062863 | A1* | 3/2006 | Ghosal | A61P 3/06 |
| | | | | 424/757 |
| 2017/0239312 | A1* | 8/2017 | Wood | A61K 36/8962 |
| 2019/0224193 | A1* | 7/2019 | Reid | A61K 38/063 |
| 2020/0268821 | A1* | 8/2020 | Leone-Bay | A61K 31/375 |

OTHER PUBLICATIONS

Karawya M. et al. Screening of Diphenylamine as an Antihyperglycaemic Agent . . . Acta Pharmaceutica Hungarica 56(2)55-58, 1986. (Year: 1986).*

Yamashita, Y. Methylxanthine Derivative Rich Cacao Extract Suppresses Differentiation of Adipocytes . . . J of Nutritional Science and Vitaminology 64(2)151-160, 2018. (Year: 2018).*

* cited by examiner

SYNERGISTIC HERBAL COMPOSITIONS FOR THE TREATMENT OF OBESITY AND OVERWEIGHT

TECHNICAL FIELD OF THE INVENTION

The invention relates to synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* and optionally containing at least one ingredient selected from pharmaceutically acceptable excipient, diluent, and carrier or mixtures thereof for obtaining at least one health benefit selected from preventing, controlling or treating obesity and/or overweight; improving lean body mass, improving the browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body. The invention also relates to a method of obtaining at least one health benefit selected from preventing, controlling or treating obesity and/or overweight; improving lean body mass, improving the browning of White Adipose Tissue (WAT)/ improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body in a human by using a suitable dose of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* and optionally containing at least one ingredient selected from pharmaceutically acceptable excipient, diluent, and carrier or mixtures thereof.

BACKGROUND OF THE INVENTION

Obesity and overweight are rapidly growing conditions in increased number of countries across the globe. As per recent WHO report, worldwide obesity has tripled since 1975. A person with a body mass index (BMI) of ≥30 kg/m² is generally considered as obese and over weight is a condition identified with a BMI of ≥25 kg/m2; both the conditions are caused by an imbalance between energy intake and expenditure. Obesity is associated with substantial increase in morbidity, premature mortality, impaired quality of life and big health care costs. Excess body weight increases the chances of developing diabetes, metabolic syndrome, hypertension, dyslipidemia, myocardial infarction, stroke, certain cancers, sleep apnea and osteoarthritis. The primary strategies to develop therapeutic agents that can reduce body weight include decreasing the consumption or absorption of food, and/or by increasing energy expenditure. Many pharmaceutical agents were commercialized as answer to the obesity problem, but most of them were withdrawn from the market owing to unacceptable side-effects. In the last few decades, researchers in the area of metabolic disorders have turned their attention towards food derived ingredients, particularly from the plant and marine worlds, in search of treatments for obesity/overweight and associated diseases. Some herbal extracts and food components have been shown to affect appetite regulation, fat oxidation, energy uptake or thermogenesis. Although herbal ingredients are known to have the advantage of fewer adverse side effects and thus may represent interesting complementary approaches to the management of obesity.

The patent publication US2016045560 A1, discloses a weight loss product comprising a mixture of *Alchemilla vulgaris, Olea europaea, Cuminum cyminum* and *Mentha longiflora* (in weight proportion 12:10:5:4) and an additional ingredients selected from *Theobroma cacao*, caffeine anhydrous, *Coffea Arabica, Coffea canephora, Camellia sinensis, Ilex paraguariensis*, Guarana, and kola nut.

The patent application WO2016046375 A1, discloses *Theobroma cacao* extract for the treatment of receptor tyrosine kinase related disorders.

The patent application WO2008110853 A1, discloses composition containing aqueous fluid extracts of leaves of *Cucumis sativus, Citrus aurantifolia, Pimenta racemosa* and *Graptophyllum pictum* for psoriasis and other dermatological diseases such as acne and mycotic diseases.

Patent publication, AU2006312947B2, disclosed a weight loss promoting diet supplement comprising at least 3% Corosolic acid, a source of Catechins and *Theobroma cacao* Extract.

Patent publication, US20100112099A1, discloses a method for activating myocyte AMPK in an animal by using composition comprising a pharmaceutically effective dose of one or more of the members of the group consisting of phytochemicals or extracts isolated from *Zingiber officinale, Cotinus coggygria, Citrus aurantium*, Lupulone, Whey protein isolate, Chromium polynicotinate, Hexahydroisoalpha acids, Xanthohumol, Rho-isoalpha acids, Sambucu, *Gymnema sylvesre, Camellia sinensis, Acacia nilotica, Malus pumila, Ribes nigrum* L., *Hypericum perforatum, Theobroma cacao, Vaccinium, Camellia sinensis, Rosa canina*, Isoalpha acids, *Vaccinium erythroCarpum*, Leucine, *Hydrastis Canadensis, Vitis vinifera, Rhamnus purshiana, Epimedium* (horny Goat Weed), *Curcuma longa, Opuntia ficus* indica, *Syzygium cumini*, and Tetrahydroisoalpha acids.

Another patent publication, U.S. Pat. No. 7,329,419B2, discloses weight-loss tablet comprising effective amounts of green tea, ginger, caffeine, cocoa, calcium, yerba mat, hawthorne berry, parsley leaf marshmallow root, fennel seed, astragalus root, licorice root, suma, cinnamon, celery seed, and alfalfa leaf.

Hence, there is a continuous need in the art to provide alternative treatments comprising highly effective herbal compositions for management of obesity and overweight. In addition, herbal extracts and compositions that are both well tolerated and more efficacious are urgently needed for addressing obesity and overweight.

OBJECT OF THE INVENTION

The object of the present invention is to provide synergistic herbal compositions comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* for obtaining at least one health benefit selected from preventing, controlling or treating obesity and/or overweight; improving lean body mass, improving the browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body.

Another object of the present invention is to provide methods of preventing, controlling or treating obesity and/or overweight; improving lean body mass, improving browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body in humans or animals, wherein the method comprises supplementing the humans with an effective dose of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*.

Yet another object of the invention is to provide use of synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* for obtaining at least one health benefit selected from preventing, controlling or treating obesity and/or overweight; improving lean body mass, improving the browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body.

SUMMARY OF THE INVENTION

The present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* for obtaining at least one health benefit selected from preventing, controlling or treating obesity and/or overweight; improving lean body mass, improving browning of the White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body.

Another aspect of the invention provides a method of obtaining a health benefit selected from preventing, controlling or treating obesity and/or overweight; improving lean body mass, improving browning of the White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body in humans wherein the method comprises supplementing the humans with an effective dose of synergistic herbal composition comprising combination of first ingredient selected from the extracts, fractions and mixtures thereof derived from *Theobroma cacao* and a second ingredient selected from the extracts, fractions, and mixtures thereof derived from *Citrus aurantifolia* and optionally comprises at least one ingredient selected from pharmaceutically acceptable excipient/diluent, and carrier thereof.

Another aspect of the invention provides the use of synergistic herbal composition comprising combination of first ingredient selected from the extracts, fractions and mixtures thereof derived from *Theobroma cacao* and a second ingredient selected from the extracts, fractions, and mixtures thereof derived from *Citrus aurantifolia* and optionally comprises at least one ingredient selected from pharmaceutically acceptable excipient/diluent, carrier and mixtures thereof for obtaining at least one health benefit selected from preventing, controlling or treating obesity and/or overweight; improving lean body mass, improving browning of the White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety/, supporting weight loss, improving fat loss and maintaining a slim body.

Other aspect of the invention provides the synergistic herbal composition comprising combination of first ingredient selected from the extracts, fractions and mixtures thereof derived from *Theobroma cacao* and a second ingredient selected from the extracts, fractions, and mixtures thereof derived from *Citrus aurantifolia* and optionally comprises at least one ingredient selected from pharmaceutically acceptable excipient/diluent, and carrier thereof for the amelioration of the metabolic processes such as promotion of lipolysis, and inhibition of adipogenesis, increase of Fibroblast growth factor-21 (FGF-21), increase of uncoupling protein (UCP-1) and increase of β3-adrenoceptors (β3-ARs).

DETAILED DESCRIPTION OF THE INVENTION

Figure 1A:
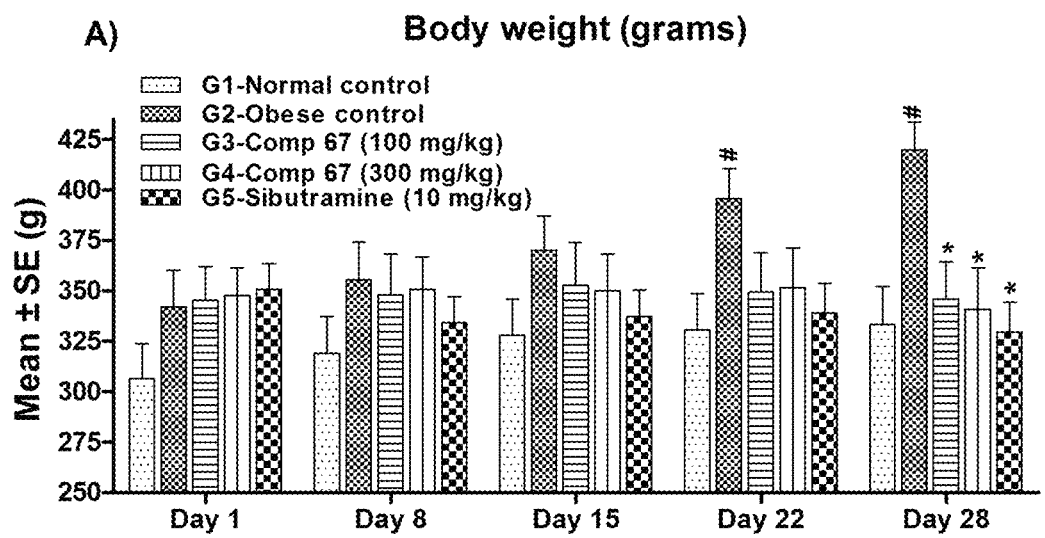
FIGS. 1A and 1B: Bar diagrams showing the body weights of animals in control and treatment groups on days 1, 8, 15, 22 and 28 (A). Each bar presents mean body weight±SM. Significant at $p<0.05$; #G1 vs. G2; *G2 vs. the treatment groups. Bar diagram shows percentage change in body weight of control and treatment groups of animals on day 28 (B). G1 and G2 represent the groups of rats supplemented with normal chow and high fat diet, respectively. G3, G4 and G5 represent high fat diet plus 100 and 300 mg/kg body weight of composition-67, and 10 mg/kg body weight of Sibutramine supplemented rats, respectively.

The invention will now be described in detail in connection with certain preferred and optional embodiments, so that various aspects thereof may be more fully understood and appreciated.

The terms 'adipolysis' and 'lipolysis' are art recognized terms and interchangeably used in throughout the specification and a skilled person will understand and appreciate the same as such. Similarly, browning, browning of fat, beige fat and browning of white adipose tissue (WAT) are also used interchangeably. The terms 'herbs' and 'plants' are also used interchangeably throughout the specification.

Adipogenesis is the process of differentiation and proliferation of pre-adipocytes into mature adipocytes or fat cells. In this process, proliferation of pre-adipocytes or precursor fat cells is followed by the differentiation of these cells to the mature adipocyte phenotype. The nuclear receptor PPAR γ is known to play a critical role in adipocyte differentiation and fat deposition. Adipocytes play a vital role in energy homeostasis and responsible for the maintaining the largest energy reserve as triglyceride in the body of animals. Adipocytes stay in a dynamic state, they start expanding when the energy expenditure exceeds the intake. This process is highly regulated by counter regulatory hormones to which these cells are very sensitive. Thus, adipogensis inhibition is one of the main targets for developing treatments against obesity/overweight and to promote slimming.

Adipolysis (Lipolysis) is the catabolic process leading to the breakdown of triglycerides stored in fat cells and release of fatty acids and glycerol into blood stream. This is highly a regulated process, which allows appropriate delivery of free fatty acids to meet energy needs. Thus, increasing adipolysis is one of the main targets for treating obesity/overweight and for promoting slimming. β3-Adrenoreceptor agonists can stimulate lipolysis in the white adipose tissue and thermogenesis in the brown adipose tissue. Plant extracts, fraction and phytochemical agents having the lipolysis activity could be useful in the treatment of obesity, over weight and other metabolic disorders.

Hence the inventors of the current application randomly screened a large number of plant extracts and fractions for their anti-adipogenesis & pro-adipolysis activities and found that the extracts and fractions derived from *Theobroma cacao* and *Citrus aurantifolia* showed a potent dose dependent anti-adipogenesis and pro-lipolysis activities as summarized in tables 3 to 7.

A brief summary on each of the plant material is provided herein below.

*Theobroma cacao*: *Theobroma cacao* L. is a small but economically important tree. It is an evergreen, 4-8 m tall tree of the Sterculiaceae family, which is native to the tropical region of the Americas. Cocao seeds are significant source of polyphenols and theobromine. The seeds are used to make cocoa mass, cocoa powder, confectionary, gouache and chocolate. The cocoa extract or its phytochemicals showed several beneficial effects against platelet aggregation, high blood pressure, atherosclerosis, hyperglycemia and hypercholesterolemia, inflammation, hepatocarcinogenesis, DNA damage and clastogenic effect. Theobromine (I) is the principle alkaloid in *Theobroma cacao* (Donald L. Pavia, *Journal of Chemical Education*, 1973, 50, 791-792) and the extracts used in the current invention are standardized to therobromine by HPLC method of analysis.

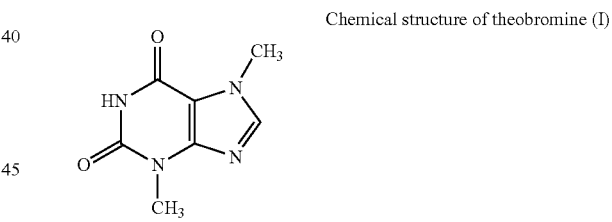

Chemical structure of theobromine (I)

*Citrus aurantifolia*: *C. aurantifolia* is a perennial evergreen tree that can grow to a height of 3-5 m. It is irregularly slender branched and possesses short and stiff sharp spines or thorns. Its flowers are short, some are white and fragrant. Its green fruit is round and 3-5 cm in diameter; it is yellow when ripe. *C. aurantifolia*'s classification: kingdom (Plantae); sub-kingdom (Tracheobionta); superdivision (Spermatophyta); division (Magnoliophyta); class (Magnoliopsida); subclass (Rosidae); order (Sapindales); family (Rutaceae); genus (*Citrus*); species (*C. aurantifolia*). It is native to the tropical and subtropical regions of Asia and Southeast Asia including India, China, and it was introduced to North Africa, Europe, and worldwide. The vernacular name of *C. aurantifolia* is lime (English). It is not only used as flavoring agents in beverages, manufactured foods, and pharmaceutical forms, but also as ingredients in perfumes. *Citrus aurantifolia* peels have been traditionally used as an anti-diabetic, anti-lipidemia, anti-insecticide, anti-cancer activities. It showed in vitro xanthine oxidase inhibitory activity, antioxidant, cytotoxic anti-viral activities. It is known to be used in cosmetic products like sun less tanning, bar soaps etc. Limonin (II) is identified as a principle metabolite in *Citrus aurantifolia* and the extracts of the current invention are standardized for Limonin (II) by HPLC method of analysis.

Chemical structure of Limonin (II)

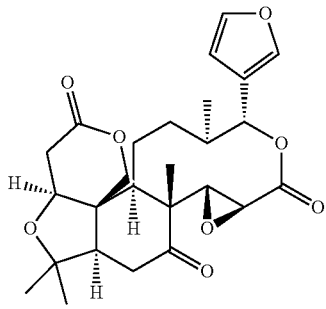

Source of the herbs used in the invention as follows:
1. *Theobroma cacao* seed was collected from cultivation source in Aswaraopeta village, Aswaraopeta panchayati, Aswaraopeta mandal, Bhadradri Kothagudem district, Telangana state.
2. *Citrus aurantifolia* was collected from cultivation source in Rayapudi village, Rayapudi panchayati, Thullur mandal, Guntur district, Andhra Pradesh state.

*Theobroma cacao* seeds were pulverized and the powder was extracted with various solvents such as water, aqueous ethanol, ethanol, aqueous methanol and n-butanol to obtain water extract (T.C-1), aqueous ethanol extract (T.C-2), ethanol extract (T.C-3), aqueous methanol extract (T.C-4) and n-butanol extract (T.C-5) respectively. The said extracts of *Theobroma cacao* seed were standardized to theobromine (I) by analytical HPLC method and the results were summarized in Table 1. Similarly, *Citrus aurantifolia* fruit peel was pulverized and the powder was extracted with various solvents such as aqueous ethanol, ethanol, water, aqueous methanol and n-butanol to obtain aqueous ethanol extract (C.A-1), ethanol extract (C.A-2), water extract (C.A-3), aqueous methanol extract (C.A-4), and n-butanol extract (C.A-5) respectively. The extracts of *Citrus aurantifolia* were standardized to Limonin (II) by analytical HPLC method and the results were summarized in Table 2.

The said *Theobroma cacao* seed extracts and *Citrus aurantifolia* fruit peel extracts were evaluated for their anti-adipogenesis & pro-adipolysis activities using in vitro cellular models in mouse 3T3-L1 pre-adipocyte cells. The results indicated that the extracts were potent in inhibiting adipogenesis and increasing adipolysis. The, *Theobroma cacao* seed water extract (T.C-1), for example, at the treatment concentrations of 5 µg/mL and 10 µg/mL showed 38.36% and 41.10% inhibition in adipogenesis respectively. The *Citrus aurantifolia* fruit peel aqueous ethanol extract (C.A-1) at the treatment concentration of 5 µg/mL and 10 µg/mL showed 25.81% and 35.74% inhibition in adipogenesis respectively. The other solvent extracts of *Theobroma cacao* seed and *Citrus aurantifolia* fruit peel were also found to be efficacious.

These individual extracts or their fractions were then evaluated to explore the feasibility of a synergistic efficacy between these ingredients. The extracts or fractions derived from *Theobroma cacao* and extracts or fractions derived from *Citrus aurantifolia* were combined at different ratios to obtain compositions-1 to 65 (C-1 to C-65). The said compositions (compositions 1-65) were tested for adipogenesis inhibition activity in comparison with the corresponding individual ingredients. The data from in vitro adipogenesis inhibition assay for these compositions unexpectedly showed better efficacy in inhibiting adipogenesis when compared to their corresponding individual ingredients suggesting that the extract(s), or fraction(s) or phytochemicals or mixtures thereof derived from *Theobroma cacao* have the tendency to exhibit synergism when combined with extract(s), or fraction(s) or phytochemicals or mixtures thereof derived from *Citrus aurantifolia*.

For example, *Theobroma cacao* seed water extract (T.C-1) at 1.67 µg/mL and *Citrus aurantifolia* fruit peel 50% aqueous ethanol extract (C.A-1) at 3.33 µg/mL concentration showed 15.23% and 19.47% inhibitions of adipogenesis respectively. The composition-2 containing *Theobroma cacao* seed water extract (T.C-1) and *Citrus aurantifolia* 50% peel aqueous ethanol extract (C.A-1) in the ratio of 1:2 at 5 µg/mL showed 44.78% inhibition of adipogenesis, which is significantly better than the additive effect 34.7% (15.23%+19.47%) calculated from the inhibitions showed by the corresponding individual ingredients. The composition-1 (C-1) and compositions-3 to 5 (C-1 and C-3 to C-5) containing these two extracts (T.C-1 and C.A-1) at ratios 1:3, 1:1, 2:1 and 3:1 respectively also exhibited synergism when compared to the inhibitions shown by each of their corresponding individual ingredient concentrations as summarized in Table 3. The other compositions (C6 to C19) containing *Theobroma cacao* seed water extract (T.C-1) in combination with other solvent extracts of *Citrus aurantifolia* peel (C.A-2-C.A-5) also showed synergistic adipogenesis inhibition (Table 3).

In an additional example, *Theobroma cacao* seed 50% aqueous ethanol extract (T.C-2) at 0.83 µg/mL and *Citrus aurantifolia* peel 50% aqueous ethanol extract (C.A-1) at 1.67 µg/mL concentration showed 2.07% and 26.46% inhibitions of adipogenesis respectively. The composition-21 containing *Theobroma cacao* seed 50% aqueous ethanol extract (T.C-2) and *Citrus aurantifolia* peel 50% aqueous ethanol extract (C.A-1) in the ratio of 1:2 at 2.5 µg/mL showed 40.19% inhibition of adipogenesis, which is significantly better than the additive effect 28.53% (2.07%+ 26.46%) calculated from the inhibitions showed by the corresponding individual ingredients. The compositions-20 and 22 to 24 (C-20, C-22 to C-24) containing these two extracts (T.C-2 and C.A-1) at other ingredient ratios and also compositions containing *Theobroma cacao* seed 50% aqueous ethanol extract (T.C-2) in combination with other solvent extracts of *Citrus aurantifolia* fruit peel also exhibited synergism when compared to the inhibitions shown by each of their corresponding individual ingredient concentrations as summarized in table 4.

Similarly, the compositions (C-39 to C-65) comprising other solvent extracts of *Theobroma cacao* and *Citrus aurantifolia* showed synergism when compared to the inhibitions shown by each of their corresponding individual ingredient concentrations as summarized in table 5.

The compositions (compositions 1-65) were further tested for their efficacy to increase adipolysis using in vitro cellular models in mouse 3T3-L1 pre-adipocyte cells in comparison with the corresponding individual ingredients. The data from in vitro adipolysis assay for these compositions unexpectedly showed better efficacy in increasing adipolysis when compared to their corresponding individual ingredients suggesting that the extract(s), or fraction(s) or phytochemicals or mixtures thereof derived from *Theobroma*

*cacao* have the tendency to exhibit synergism when combined with extract(s), or fraction(s) or phytochemicals or mixtures thereof derived from *Citrus aurantifolia*.

For example, *Theobroma cacao* seed water extract (T.C-1) at 6.67 μg/mL and *Citrus aurantifolia* fruit peel 50% aqueous ethanol extract (C.A-1) at 13.33 μg/mL concentration showed 29.52% and 7.12% increase of adipolysis respectively. The composition-2 containing *Theobroma cacao* seed water extract (T.C-1) and *Citrus aurantifolia* peel 50% aqueous ethanol extract (C.A-1) in the ratio of 1:2 at 20 μg/mL showed 47.88% increase of adipolysis, which is significantly better than the additive effect 36.64% (29.52%+7.12%) calculated from the increase showed by the corresponding individual ingredients. The composition-1 & compositions-3 to 5 containing these two extracts (T.C-1 and C.A-1) at other ingredient ratios also exhibited synergism when compared to the increase shown by each of their corresponding individual ingredient concentrations as summarized in Table 6.

The other compositions (C6 to C19) containing *Theobroma cacao* water extract (T.C-1) and other solvent extracts of *Citrus aurantifolia* (C.A-2-C.A-5) also showed synergistic pro-adipolysis activity (Table 6). Similarly, compositions (C-20 to C-65) comprising other solvent extracts of *Theobroma cacao* and *Citrus aurantifolia* showed synergism when compared to the increase shown by each of their corresponding individual ingredient concentrations as summarized in Table 7.

Interestingly, the extracts and fractions derived from *Theobroma cacao* seed and *Citrus aurantifolia* fruit peel and their compositions further exhibited unexpected efficacy in other mechanisms for addressing obesity and overweight, such as fat browning, thermogenesis, resting energy expenditure, improving thyroid function, increasing satiety, modulation of molecular factors responsible for browning of white fat cells such as FGF21, UCP-1 and β3-AR, as discussed below.

Brown Adipose Tissue (BAT), Browning of White Adipose Tissue (WAT) and Resting Energy Expenditure: Adipose tissue (body fat) is a loosely bound connective tissue composed of adipocytes, which are derived from pre-adipocytes. In humans, adipose tissue is located mainly beneath the skin (subcutaneous fat) and around internal organs (visceral fat). White adipose tissue (WAT), also called as white fat, is one of the two types of adipose tissue found in mammals. The other kind of adipose tissue is Brown Adipose Tissue (BAT). White adipose tissue stores energy in the form of lipids and it undergoes pathological expansion during obesity. Brown adipose tissue (BAT) is a specialized form of adipose tissue in humans and other mammals. BAT evolved in mammals to dissipate large amounts of chemical energy as heat through a process called thermogenesis. BAT is not only an important body defense against hypothermia but also plays a role in diet-induced thermogenesis. Brown fat cells possess large numbers of mitochondria, which are equipped with a specialized protein known as uncoupling protein 1 (UCP-1). UCP-1 short-circuits the electron transport chain, which is otherwise normally used to drive the synthesis of cellular ATP, and thus allowing mitochondrial membrane potential to be transduced to heat (thermogenesis), thus making BAT a tissue capable of altering energy expenditure and fuel metabolism without an increase in physical activity.

In recent years, the topic of brown adipose tissue has been reinvigorated with many new studies pertaining to conversion of White Adipose Tissue (WAT) to Beige fat, also known as WAT browning. WAT from certain depots, in response to appropriate stimuli, can undergo a process known as "browning" to produce beige fat, where it takes on characteristics of BAT, by increasing specific protein expression such as UCP-1, the presence of multilocular lipid droplets and multiple mitochondria. The beige adipocytes induced by the 'browning' stimulus are phenotypically similar to the classical brown adipocytes in BAT with comparable amounts of mitochondria and UCP-1, thus indicating that they may have similar thermogenic capacities as BAT. The fibroblast growth factor 21 (FGF21) plays a physiologic role in thermogenic recruitment of WATs and it is also an important regulator of browning. Peroxisome Proliferator Activated Receptor gamma co-activator 1 alpha (PGC 1α) is also one of the important regulator of transcription central to WAT browning. Also, white adipose tissue browning is driven by sympathetic stimulation through involvement of norepinephrine (NE) with β3-adrenergic receptors (β3AR) of white adipocytes. The β3AR activation starts a signal transduction cascade that results in overexpression of UCP-1 and other thermogenic proteins in the white fat cells. This series of events are part of the browning of white fat cells through the intermediate stage, beige or brite cells. In addition, the thyroid hormone, specifically T3 positively regulates UCP-1 synthesis. T3 can independently stimulate the UCP-1 synthesis or can work in cooperation with sympathetic stimulation in a synergistic manner. The activity of T3 is inhibited by T4. Therefore, a healthy balance between T3 and T4 is crucial for browning of the white fat cells.

FGF-21: Fibroblast Growth Factor-21 (FGF-21) is a novel member of the FGF family and is predominantly expressed in liver. FGF-21 is involved in the control of metabolism by modulating glucose homeostasis, insulin sensitivity, ketogenesis, and promoting adipose tissue "browning." During the past decade, FGF-21 has been shown to be a potential therapeutic target for the treatment of obesity and diabetes. Adipose tissue is one of the main targets of FGF-21 action and one of the important metabolic benefit of FGF-21 is "browning". Growing body of evidence suggests that FGF-21 plays a physiologic role in thermogenesis and thermogenic recruitment of white adipose tissue through up-regulating the expression of UCP-1 and other thermogenic genes by an autocrine-paracrine axis. FGF21 also enhances PGC 1α levels in fat tissues.

A few compositions selected from among compositions-1 to composition-65 were tested in comparison with the corresponding individual ingredients for their ability to increase the Fibroblast Growth Factor-21 (FGF-21) in cellular assay in mouse 3T3-L1 pre-adipocyte cells. The data from the in vitro FGF-21 assay for these compositions unexpectedly showed better efficacy in increasing FGF-21, when compared to their corresponding individual ingredients suggesting that the extract(s), or fraction(s) or phytochemicals or mixtures thereof derived from *Theobroma cacao* have the tendency to exhibit synergism when combined with extract(s), or fraction(s) or phytochemicals or mixtures thereof derived from *Citrus aurantifolia*.

For example, *Theobroma cacao* seed water extract (T.C-1) at 1.67 μg/mL and *Citrus aurantifolia* fruit peel 50% aqueous ethanol extract (C.A-1) at 3.33 μg/mL concentration showed 10.08% and 18.60% increase of FGF-21 respectively. The composition-2 containing *Theobroma cacao* water extract (T.C-1) and *Citrus aurantifolia* 50% aqueous ethanol extract (C.A-1) in the ratio of 1:2 at 5 μg/mL showed 44.21% increase of FGF-21, which is significantly better than the additive effect 28.68% (10.08%+18.60%) calculated from the increase showed by the corresponding individual ingredients. The compositions-1 and compositions-3 to 5 containing these two extracts (T.C-1 and C.A-1) at other ingredient ratios also exhibited synergism when compared to the inhibitions shown by each of their corresponding individual ingredient concentrations as summarized in Table 8. The other compositions (C-10 and C-15) containing *Theobroma cacao* water extract (T.C-1) and other solvent extracts of *Citrus aurantifolia* (C.A-2-C.A-5) and the compositions-20 to 23 and compositions-36 to 38 (C-20 to C-23 & C36 to 38) containing other solvent extracts of *Theobroma cacao* seed and *Citrus aurantifolia* peel also showed synergistic increase in FGF21 activity when compared to the increase shown by each of their corresponding individual ingredient concentrations as summarized in Table 8.

UCP-1: The worldwide epidemic of obesity and other metabolic disorders drove the scientific community to focus the attention recently on white adipose tissue (WAT) and its biology. WAT can be converted into brown fat-like tissue under certain physiological and pathophysiological situations. The phenomenon of white fat "browning," in which certain white adipose tissue depots significantly increase gene expression for the uncoupling protein (UCP-1) and thus supposedly acquire thermogenic and fat-burning properties, has attracted considerable attention as it changes their function from energy storage to energy dissipation. UCP-1 is an integral membrane protein found in the mitochondrial inner membrane of brown adipose tissue, and facilitates the process of non-shivering thermogenesis in mammals. Hence, major focus of the researchers is to identify agents that would induce a "browning" response, increase the expression and activity of UCP-1 in adipose tissues, which ultimately help to counteract the development of obesity and overweight; and other metabolic disorders and promote energy expenditure.

Hence, a few selected compositions among compositions-1 to 65 were tested for uncoupling protein (UCP-1) expression activity in cellular models using mouse 3T3-L1 pre-adipocyte cells. The data from in vitro UCP-1 assay for these compositions unexpectedly showed significant increase in UCP-1 expression, over the control. For example, the compostions-1 to 5 containing *Theobroma cacao* seed water extract (T.C-1) and *Citrus aurantifolia* fruit peel 50% aqueous ethanol extract (C.A-1) at 1:3, 1:2, 1:1, 2:1 and 3:1 ratios showed significant efficacy with 38.48%, 34.23%, 33.81%, 30.71% and 28.69% increase UCP-1 expression respectively over the control. Similarly, the compostions-58 and 59 containing *Theobroma cacao* seed 50% methanol extract (T.C-4) and *Citrus aurantifolia* fruit peel 50% aqueous ethanol extract (C.A-1) at 1:1 and 2:1 ratio also exhibited significant improvement with 24.63% and 11.96% increase in UCP-1 expression over the control. The data summarized in Table 9 thus suggests that the compositions containing extracts or fraction derived from *Theobroma cacao* and extracts or fractions derived from *Citrus aurantifolia* can have the potential to up-regulate UCP-1 expression, which in turn correlates to increased fat browning, thermogenesis and resting energy expenditure.

β3AR: β3-AR is a beta-adrenergic receptor located primarily in adipose tissue. Its main actions include regulation of lipolysis and thermogenesis. Classical BAT depots are highly innervated and are activated by centers in the brain in responsive to certain stimuli such as cold exposure and exposure to certain chemicals from diet, leading to the release of norepinephrine (NE) from sympathetic nerves. Upon binding of NE to BAT β3-adrenoceptors (β3-ARs), the increased levels of intracellular cyclic AMP (cAMP) promote lipolysis, and this breakdown of triglycerides leads to release of free fatty acids that upregulate and activate uncoupling protein-1 (UCP-1). Activated UCP-1 uncouples mitochondrial respiration leading to heat generation, thus β3-AR signaling increases respiration and non-shivering thermogenesis, with BAT adipocytes being remarkably rich in mitochondria. In addition to classical brown adipocytes (BAT), beige or brite adipocytes can also show similar effects. These cells reside in WAT depots but can be "browned" by various stimuli, most notably cold exposure or activators of β-AR signaling, and by the peroxisome proliferator-activated receptor (PPARγ) agonists such as rosiglitazone. Activation of brite/beige adipocytes leads to an increase in mitochondrial uncoupling similar to that occurring in BAT. Hence activation of β3-adrenergic receptor (AR) can lead to increase in browning, thermogenesis and resting energy expenditure (REE).

Hence, a few representative compositions selected from compositions-1 to 65, were tested for increase of β3-adrenoceptors (β3AR) expression in adipocyte cells. In the β3AR assay, the 3T3-L1 cells treated in vitro with the compositions unexpectedly showed significant increasing in β3AR expression over the cells treated with control as summarized in Table 10. For example, the compositions-1, 2 and 3 (C-1, C-2 and C-3) containing *Theobroma cacao* water extract (T.C-1) and *Citrus aurantifolia* peel 50% aqueous ethanol extract (C.A-1) at 1:3, 1:2 and 1:1 ratios showed 36.17%, 37.47% and 51.02% increase in β3AR expression respectively over the control. Similarly, the compositions-21 & 22 (C-21 & C-22) containing *Theobroma cacao* 50% ethanol extract (T.C-2) and *Citrus aurantifolia* 50% aqueous ethanol extract (C.A-1) at 1:2 and 1:1 ratio also showed 18.75%, and 12.66% increase in β3AR expression respectively over the control as summarized in Table 10. These results suggest that the compositions containing an extract derived from *Theobroma cacao* in combination with an extract derived from *Citrus aurantifolia* can increase the expression of β3AR and as such can have the ability to increase the fat browning, thermogenesis and lipolysis.

Formulations: The present invention also provides synergistic herbal compositions comprising at least one ingredient selected from extracts, fractions and phytochemicals or mixtures thereof derived from *Theobroma cacao* and the second ingredient selected from extracts, fractions and phytochemicals or mixtures thereof derived from *Citrus aurantifolia* and optionally containing at least one component selected from pharmaceutically or nutraceutically or dietically acceptable excipients, carriers and diluents.

The compositions comprising at least one ingredient selected from extracts, fractions and phytochemicals or mixtures thereof derived from *Theobroma cacao* and the second ingredient selected from extracts, fractions and phytochemicals or mixtures thereof derived from *Citrus aurantifolia* and optionally containing at least one component selected from pharmaceutically or nutraceutically or dietically acceptable excipients, carriers and diluents; for preventing or controlling or treating obesity, overweight and improving lean body mass, maintaining body weight and maintaining a slim body; wherein the pharmaceutically or nutraceutically or dietically acceptable excipients, carriers and diluents are selected from monosaccharide's such as glucose, dextrose, fructose, galactose etc.; Disaccharides such as but not limited to sucrose, maltose, lactose, lactulose, trehalose cellobiose, chitobiose etc.; Polycarbohydrates such as Starch and modified starch such as Sodium starch glycolate, pre-gelatinized starch, soluble starch, and other modified starches; Dextrins that are produced by hydrolysis of starch or glycogen such as yellow dextrin, white dextrin, Maltodextrin etc.; Polyhydric alcohols or sugar alcohols such as but not limited to Sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to NEUSILIN, VEEGUM Talc, colloidal silicon dioxide etc.; metallic stearates such as but not limited to calcium stearate, magnesium stearate, zinc Stearate etc.; Organic acids such as citric acid, tartaric acid, malic acid, succinic acid, lactic acid, L-ascorbic acid etc.; Fatty acid esters and esters of poly sorbate, natural gums such as but not limited to *acacia*, carrageenan, Guar gum, Xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc Sulphate, zinc chloride etc.; Natural pigments, flavors, Class I & Class II preservatives and aqueous, alcoholic, hydro-alcoholic, organic solutions of above listed ingredients alone or in combination.

For example, the composition-66 was prepared by combining 60 g of *Theobroma cacao* seed water extract (T.C-1), 30 g of *Citrus aurantifolia* fruit peel 50% aqueous ethanol extract (C.A-1), 9 g of maltodextrin and 1 g of syloid. Similarly, the composition-67 was prepared by combining 53.33 g of *Theobroma cacao* seed water extract (T.C-1), 26.67 g of *Citrus aurantifolia* fruit peel 50% aqueous ethanol extract (C.A-1), 18 g of maltodextrin and 2 g of syloid in presence of ethanol/water followed by drying. Further, the composition-68 was prepared by combining 53.2 g of *Theobroma cacao* seed water extract (T.C-1), 26.6 g of *Citrus aurantifolia* fruit peel 50% aqueous ethanol extract (C.A-1), 18.2 g of glucidex-12D and 2 g of syloid in presence of ethanol/water followed drying to give the composition.

Figure 1B:
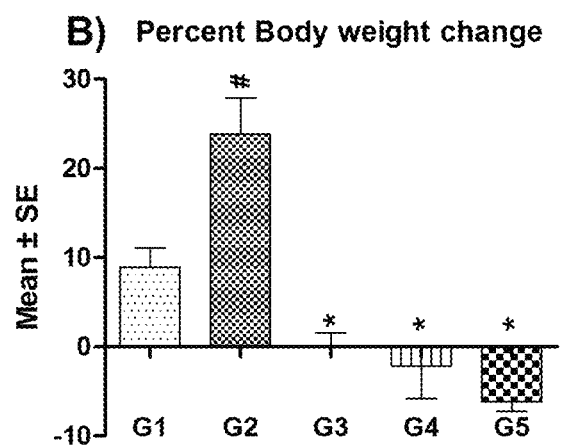

In-vivo evaluation of composition-67 in High Fat Diet (HFD) induced obese animals: The potent anti-obesity properties and synergistic effects shown by the compositions comprising *Theobroma cacao* and *Citrus aurantifolia* in in vitro models were further evaluated in an in vivo model of obesity. Obesity was induced in male Sprague Daley rats by supplementing the rats with High Fat diet for four weeks. Control group (G1) was fed with normal chow. After four weeks of induction period, the obese rats were randomly allocated to various groups G2 to G4 with seven animals in each group and the animals belonged to the treatment groups were orally supplemented daily with 100 mg/kg (G3) or 300 mg/kg (G4) body weight of the composition-67 or 10 mg sibutramine (G5) each in 10 mL of 0.5% CMC in water for further four weeks. The control group (G2) of animals received only the vehicle (10 mL of 0.5% CMC in water). Body weight of individual animal was recorded weekly, and mean body weight of the animals in each group was determined. The body weight gain/change was calculated at the end of $1^{st}$ week, $2^{nd}$ week, $3^{rd}$ week and 4th week after initiation of treatment in comparison to respective initial body weight. Composition-67 significantly and dose dependently inhibited the body weight gain in high fat diet induced obese rats when compared to HFD control group (G2). It exhibited 99.5% and 109.1% reduction in body weight gain in the treatment group supplemented with 100 mg/kg and 300 mg/Kg body weight of Composition-67 respectively at the end of treatment period. However, the effect started to show significance by 2 weeks of treatment in 300 mg/Kg dose group. The results of body weight and final percent body weight change for the treatment groups and control group are summarized in FIGS. 1A and 1B. These results clearly suggest that Composition-67 has potent anti-obesity effect.

In addition, the daily average food intake for the group G3 and G4 rats supplemented with composition 67 were significantly reduced. The food consumption data are presented as daily dietary calorie intake (KJ/day) in FIG. 2. Together, these observations demonstrate that oral supplementation of composition-67 significantly reduces body weight gain and helps maintain healthy body weight of the HFD rats; and also restricts dietary calorie consumption by the rats.

Figure 3:
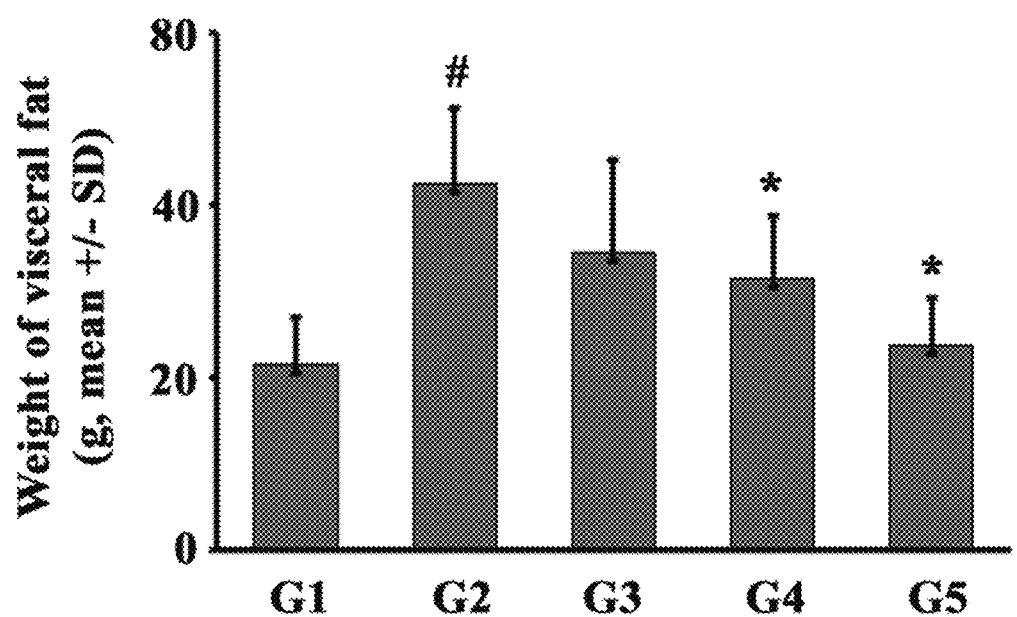
FIG. 3: Bar diagram depicts the reduction of visceral fat weight in the diet induced obese rats supplemented with Composition 67. Each bar presents mean±SD. G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. n=7; Significant at $p<0.05$; #G1 vs. G2; *G2 vs. the treatment groups.
Figure 4:
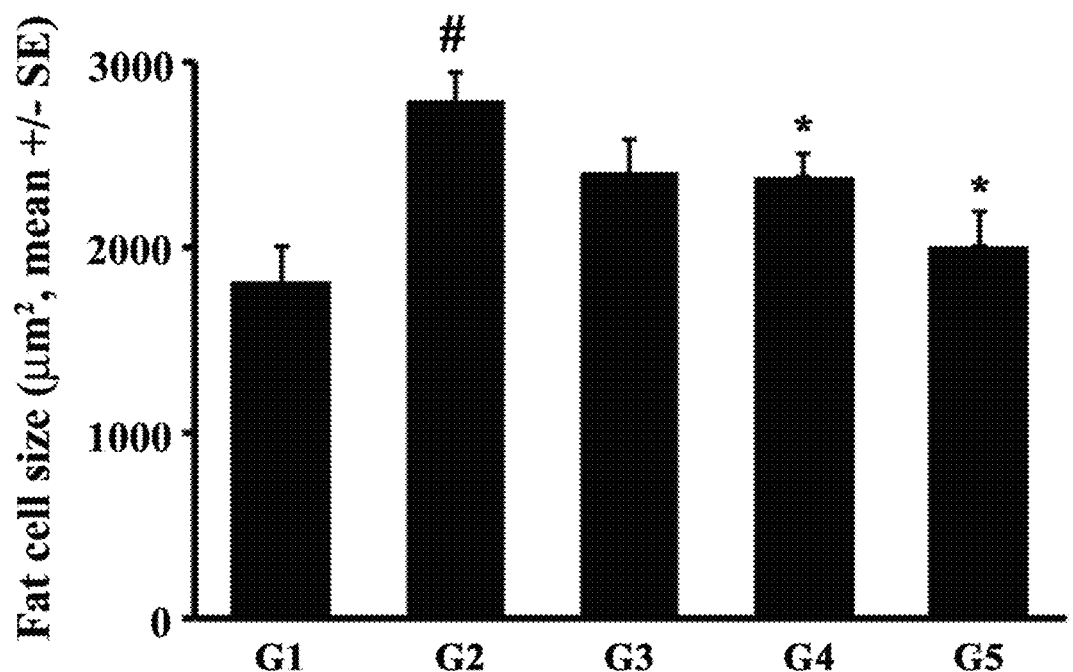
FIG. 4: Bar diagram depicts modulation of epididymal fat cell sizes in diet induced obese rats supplemented with Composition 67. Each bar presents mean±SE of the fat cell area in μm2. G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. n=7; Significant at p<0.05; #G1 vs. G2; *G2 vs. the treatment groups.

Following euthanasia at the end of the study, the visceral (retroperitoneal, epidydymal, peri-renal and mesenteric) fat tissues were collected from the rats and weighed. The total fat weight of the groups supplemented with composition-67 was significantly reduced and the group supplemented with 300 mg of composition-67 (G4) exhibited statistical significance, when compared with the HFD fed rats (FIG. 3). In addition, the microscopic examination of the paraffin-embedded-formalin fixed fat tissues revealed that the group G4 supplemented with 300 mg of composition-67 for 28 days substantially reduced the fat cell size, when compared with the HFD control group (G2) rats (FIG. 4). Collectively, these observations demonstrate that composition-67 supplementation significantly reduces the body adiposity or body fat in the obese rats.

Figure 5:
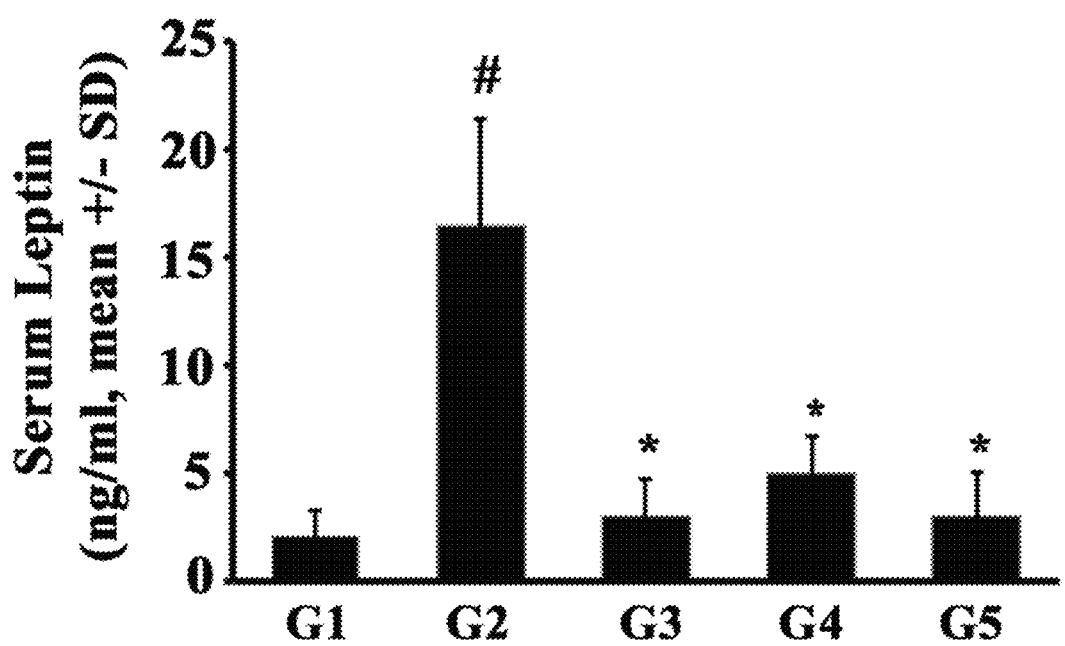
FIG. 5: Bar diagram shows normalization of the serum leptin level in the diet induced obese rats supplemented with Composition 67. G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. n=7; Significant at p<0.05; #G1 vs. G2; *G2 vs. the treatment groups.

After 28 days of supplementation, the serum samples were analyzed for circulating leptin levels. The serum leptin levels were significantly reduced in treatment groups supplemented with composition-67 in comparison with that of HFD rats as summarized in FIG. 5. Interestingly, the leptin levels in the treatment groups were reduced to the values of the chow fed control animals. This data indicates that composition-67 has a potential role in regulating food consumption via modulating satiety. This observation might explain the basis of the reduced quantity of feed consumption by the composition-67 supplemented rats in the study.

Figure 6:
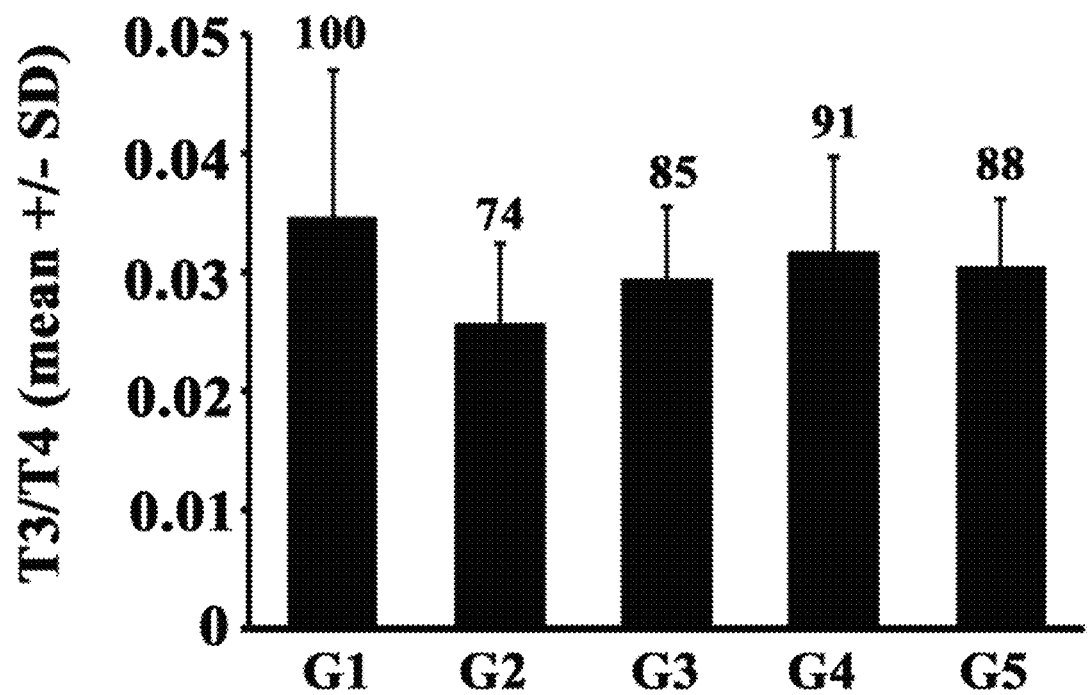
FIG. 6: Bar diagram shows improvements in the thyroid hormone balance in the diet induced obese rats supplemented with Composition 67. Each bar presents mean±SD of the ratio between triiodothyronine (T3) and thyroxine (T4). G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. n=7; the numbers above each bar represent percentage of relative T3/T4 ratio, considering 100% in G1.
Figure 7:
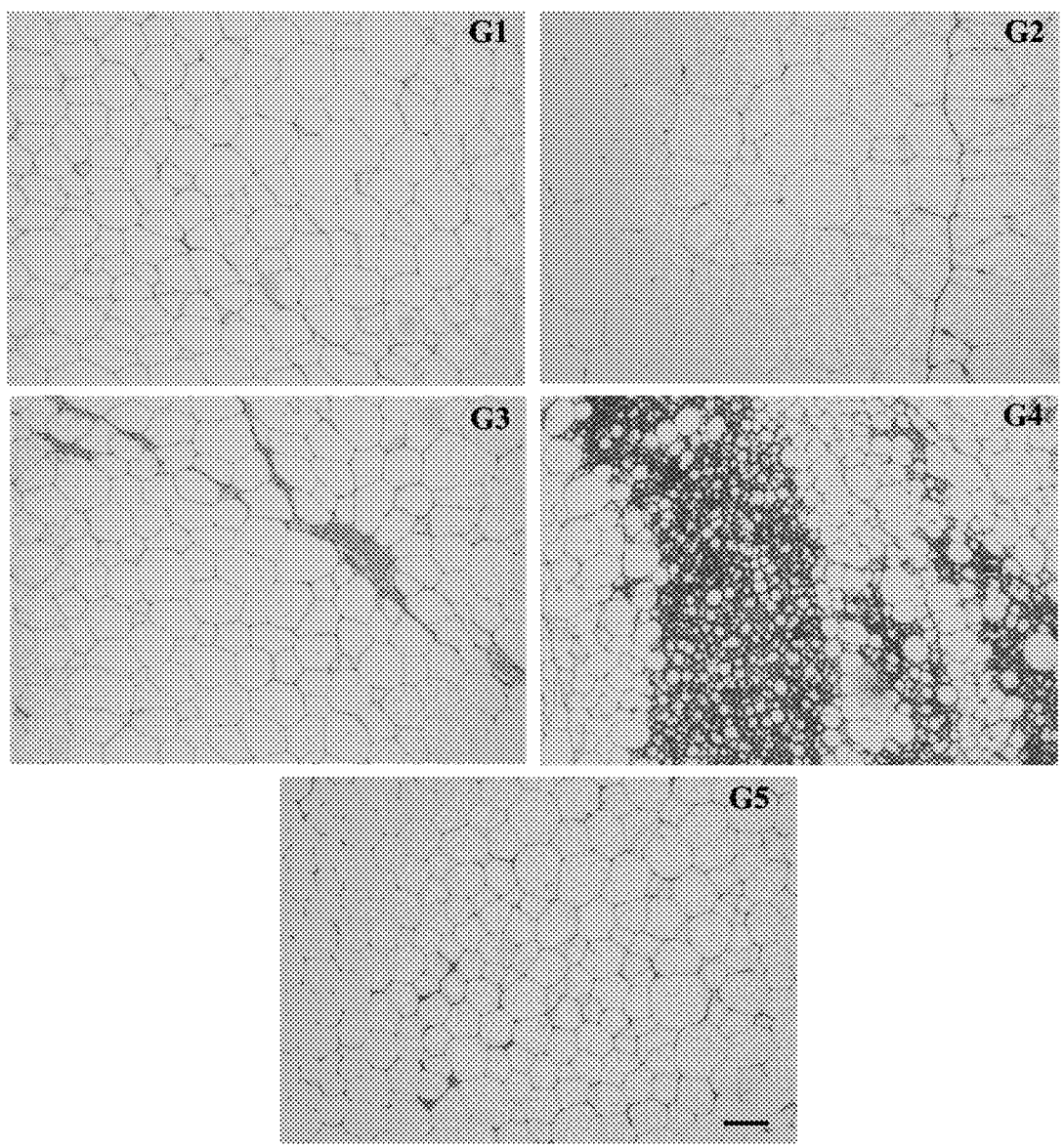
FIG. 7: Photomicrographs show immunohistochemical staining of UCP-1 in epididymal fat tissue. G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. Bar: 50 μm.

In addition, one interesting observation is that the composition-67 supplemented rats showed improved T3/T4 balance, when compared with the HFD rats (FIG. 6). T3 is the active thyroid hormone which is formed through a metabolic conversion from its precursor T4. T3 is a major regulator of energy homeostasis in the body; it positively influences the basal metabolic rate of the body or the resting energy expenditure. Besides, T3 is also a crucial factor for the white to brown fat cells transformation process. In obese animals, the T3/T4 ratio is lesser than in the non-obese individuals. In our experiment, the composition-67 supplemented rats showed improved T3/T4 ratio, when compared with the HFD rats. This observation indicates that the herbal composition improved thyroid function in the obese rats. Together, the observations strongly propose that composition-67 supplementation induced brown fat generation in conjunction with improved thyroid function; collectively, these events provided the basis of body fat reduction via increasing the resting energy expenditure in the obese rats. The immunohistochemistry study on the epididymal fat tissue demonstrates the presence of UCP-1 stained brown fat cells in composition-67 supplemented rats (FIG. 7). The chow fed (G1) or HFD (G2) rats did not show the presence of brown fat cells in their epididymal fat tissues. Therefore, the present observation clearly indicates that composition-67 potentially induces brown fat generation.

The forgoing demonstrates that synergistic herbal compositions comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* inhibit adipogenesis, accelerate lipolysis, increase the production of FGF21, increase the expression of UCP-1, β3-AR increase the browning of fat and improve T3/T4 balance. Hence, the said compositions can be useful for obtaining at least one health benefit selected from preventing, controlling or treating obesity and/or overweight; improving lean body mass, improving the browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body.

Therefore, an important embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* for obtaining at least one health benefit selected from preventing, controlling or treating obesity and/or overweight; improving lean body mass, improving browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body.

In another embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; wherein the concentration of the first ingredient in the composition varies in the range of 10%-90% by weight and the concentration of the second ingredient varies in the range of 90%-10% by weight.

In other exemplary embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* and optionally comprises at least one component selected from pharmaceutically or nutraceutically or dietically acceptable excipients, carriers and diluents.

In another embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia* and optionally comprises at least one component selected from pharmaceutically or nutraceutically or dietically acceptable excipients, carriers and diluents; for obtaining at least one health benefit selected from preventing, controlling or treating obesity and/or overweight; improving lean body mass, improving browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body; wherein the pharmaceutically or nutraceutically or dietically acceptable excipients, carriers and diluents are selected from monosaccharide's such as glucose, dextrose, fructose, galactose etc.; Disaccharides such as but not limited to sucrose, maltose, lactose, lactulose, trehalose cellobiose, chitobiose etc.; Polycarbohydrates such as Starch and modified starch such as Sodium starch glycolate, pre gelatinized starch, soluble starch, and other modified starches; Dextrins that are produced by hydrolysis of starch or glycogen such as yellow dextrin, white dextrin, Maltodextrin etc.; Polyhydric alcohols or sugar alcohols such as but not limited to Sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to NEUSILIN, VEEGUM Talc, colloidal silicon dioxide etc.; metallic stearates such as but not limited to calcium stearate, magnesium stearate, zinc Stearate etc.; Organic acids such as citric acid, tartaric acid, malic acid, succinic acid, lactic acid, L-ascorbic acid etc.; Fatty acid esters and esters of poly sorbate, natural gums such as but not limited to *acacia*, carrageenan, Guar gum, Xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc Sulphate, zinc chloride etc.; Natural pigments, flavors, Class I & Class II preservatives and aqueous, alcoholic, hydro-alcoholic, organic solutions of above listed ingredients alone or in combination.

In another embodiment, the invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*, wherein the extract or fraction is obtained from at least one plant part selected from the group comprising leaves, stems, tender stems, tender twigs, aerial parts, whole fruit, fruit peel rind, seeds, flower heads, root, bark, hardwood or whole plant or mixtures thereof.

In another embodiment, the invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*, wherein the extract or fraction is produced using at least one solvent selected from the group comprising C1-C5 alcohols like ethanol, methanol, n-propanol, isopropyl alcohol; ketones like acetone, methyl isobutyl ketone, chlorinated solvents like methylene dichloride and chloroform, water and mixtures thereof; C1-C7 hydrocarbons such as hexane; esters like ethyl acetate and the like and mixtures thereof.

In the other embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*, wherein the extracts or fractions are standardized to at least one phytochemical reference marker compound or biological active marker in the extract or fraction; wherein phytochemical marker compound or group of phytochemical compounds is in the concentration range of 0.1% to 99% by weight of the extract.

In another embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; wherein the extracts or fractions, phytochemicals of *Theobroma cacao* are standardized to theobromine; wherein theobromine is in the concentration range of 0.1% to 20% by weight of the composition.

In another embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; wherein the extracts or fractions of *Citrus aurantifolia* are standardized to Limonin; wherein Limonin is in the concentration range of 0.1% to 10% by weight of the composition.

In another embodiment, the present invention provides synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; where in the composition(s) are formulated into a dosage form selected from dry powder form, liquid form, beverage, food product, dietary supplement or any suitable form such as tablet, a capsule, a soft chewable or gummy bear.

In another embodiment of the invention, the composition(s) as disclosed above can be formulated into nutritional/dietary supplements that can be contemplated/made into the dosage form of healthy foods, or food for specified health uses such as solid food like chocolate or nutritional bars, semisolid food like cream, jam, or gel or beverage such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In a further embodiment, the present invention provides methods of preventing, controlling or treating obesity and/or overweight; improving lean body mass, improving browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body, wherein the method comprises supplementing the subject with a suitable dose of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; and optionally containing at least one additional ingredient selected from pharmaceutically acceptable excipient, diluent, and carrier.

In another embodiment, the present invention provides methods of preventing, controlling or treating obesity and/or overweight; improving lean body mass, improving browning of White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body, wherein the method comprises supplementing the subject with a suitable dose of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; and optionally containing at least one additional ingredient selected from pharmaceutically acceptable excipient, diluent, and carrier; wherein the said treatment of obesity comprises at least one of; promoting lipolysis, inhibiting adipogenesis, lipid accumulation, Increase of Fibroblast growth factor-21 (FGF-21), increase of uncoupling protein (UCP-1) and increase of β3-adrenoceptors (β3-ARs).

In another embodiment, the present invention provides use of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; and optionally containing at least one additional ingredient selected from pharmaceutically acceptable excipient, diluent, and carrier for obtaining at least one health benefit selected from preventing, controlling or treating obesity and/or overweight; improving lean body mass, improving browning of the White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body.

In another embodiment, the present invention provides method of preventing, controlling or treating obesity and/or overweight; improving lean body mass, improving browning of the White Adipose Tissue (WAT)/improving formation of brown adipose tissue (BAT), increasing basal metabolic rate (BMR)/resting energy expenditure, increasing thermogenesis, improving thyroid function, maintaining healthy body weight, increasing satiety, supporting weight loss, improving fat loss and maintaining a slim body, wherein the method comprises supplementing the subject with a suitable dose of a synergistic herbal composition comprising combination of first ingredient selected from the extracts, fractions, phytochemicals and mixtures thereof derived from *Theobroma cacao* and a second ingredient selected from the extracts, fractions, phytochemicals and mixtures thereof derived from *Citrus aurantifolia*; and optionally containing at least one additional ingredient selected from pharmaceutically acceptable excipient, diluent, and carrier; wherein supplementing the subject with a suitable dose is in the form controlled release tablets or using controlled release polymer-based coatings by the techniques including nanotechnology, microencapsulation, colloidal carrier systems and other drug delivery systems for obtaining the desired therapeutic benefit.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

Example 1: Preparation of *Theobroma cacao* Seed Water Extract

*Theobroma cacao* dried seeds (100 g) were pulverized and the powder raw material was extracted with water (700 mL) in a lab extractor at room temperature (rt) for 1 h. The extract was filtered and the spent raw material was re-extracted twice with water (2×500 mL) under similar conditions. The combined extract was filtered and concentrated under vacuum to obtain a residue of water extract as a powder (T.C-1; 14 g).

Example 2: Preparation of *Theobroma cacao* Seed Ethanol and 50% Aqueous Ethanol Extracts

*Theobroma cacao* dried seeds (100 g) were pulverized and the powder raw material was extracted with 50% aqueous ethanol (700 mL) in a lab extractor at rt for 1 h. The extract was filtered and the spent raw material was re-extracted twice with 50% aqueous ethanol (2×500 mL) under similar conditions. The combined extract was filtered and concentrated under vacuum to obtain a residue of ethanol extract (T.C-2; 11 g).

The ethanol extract (T.C-3; 4.4 g) of *Theobroma cacao* seeds (100 g) was obtained by adopting similar procedure as described above using ethanol as extraction solvent.

Example 3: Preparation of *Theobroma cacao* Seed 50% Aqueous Methanol Extract

*Theobroma cacao* dried seeds (100 g) were pulverized and the powder raw material was extracted with 50% aqueous methanol (700 mL) in a lab extractor at rt for 1 h. The extract was filtered and the spent raw material was re-extracted twice with 50% methanol (2×500 mL) under similar conditions. The combined extract was filtered and concentrated under vacuum to obtain a residue of 50% aqueous methanol extract (T.C-4; 10 g).

Example 4: Preparation of *Theobroma cacao* Seed n-Butanol Extract

*Theobroma cacao* dried seeds (100 g) were pulverized and the powder raw material was extracted with n-butanol (700 mL) in a lab extractor at rt for 1 h. The extract was filtered and the spent raw material was re-extracted twice with n-butanol (2×500 mL) under similar conditions. The combined extract was filtered and concentrated under vacuum to obtain a residue of n-butanol extract (T.C-5; 24.5 g).

Example 5: Standardization of *Theobroma cacao* Seed Extracts

The various extracts of *Theobroma cacao* seed were standardized to Theobromine by analytical HPLC method and the results were summarized in Table 1.

TABLE 1

| S. No. | Extract code | Solvent for extraction | Weight of the product | Theobromine (HPLC) |
|---|---|---|---|---|
| 1 | T.C-1 | water | 14 g | 4.4% |
| 2 | T.C-2 | 50% ethanol | 11 g | 6.9% |
| 3 | T.C-3 | Ethanol | 4.4 g | 7.5% |
| 4 | T.C-4 | 50% methanol | 10 g | 6.9% |
| 5 | T.C-5 | n-butanol | 24.5 g | 0.26% |

Example 6: Preparation of *Citrus aurantifolia* Fruit Peel 50% Aqueous Ethanol & Ethanol Extracts

*Citrus aurantifolia* dried fruit peel raw material (100 g) was pulverized in to powder and extracted with 1:1 ethanol/water (700 mL) in a lab extractor at rt for 1 h. The extract was filtered and the spent raw material was re-extracted twice with 1:1 ethanol/water (2×500 mL) under similar conditions of extraction. The combined extract was filtered and concentrated under vacuum to obtain a residue of 50% aqueous ethanol as a brown color powder (C.A-1; 21 g); Total flavonoids by UV: 9.92%.

The ethanol extract (C.A-2; 9.5 g) was obtained by adopting similar procedure using ethanol as extraction solvent.

Similarly, *Citrus aurantifolia* dried whole fruit raw material (100 g) was subjected to similar extraction procedure described above to obtain 50% aqueous alcohol extract as a brown color powder (15 g).

Example 7: Preparation of *Citrus aurantifolia* Fruit Peel Water Extract

*Citrus aurantifolia* dried fruit peel (100 g) was pulverized and the powder raw material was extracted with water (700 mL) in a lab extractor at rt for 1 h. The extract was filtered and the spent raw material was re-extracted twice with water (2×500 mL) under similar extract conditions. The combined extract was filtered and concentrated under vacuum to obtain a residue of water extract as a brown color powder (C.A-3; 21 g).

Example 8: Preparation of *Citrus aurantifolia* Fruit Peel 50% Aqueous Methanol Extract

*Citrus aurantifolia* dried fruit peel (100 g) was pulverized and the powder raw material was extracted with 50% aqueous methanol (700 mL) in a lab extractor at rt for 1 h. The extract was filtered and the spent raw material was re-extracted twice with 50% aqueous methanol (2×500 mL) under similar conditions. The combined extract was filtered and concentrated under vacuum to obtain a residue of 50% aqueous methanol extract as a brown color powder (C.A-4; 30 g).

Example 9: Preparation of *Citrus aurantifolia* Fruit Peel Butanol Extract

*Citrus aurantifolia* dried fruit peel (100 g) was pulverized and the powder raw material was extracted with n-butanol (700 mL) in a lab extractor at rt for 1 h. The extract was filtered and the spent raw material was re-extracted twice with n-butanol (2×500 mL) under similar conditions. The combined extract was filtered and concentrated under vacuum to obtain a residue of butanol extract as a brown color powder (C.A-5; 7 g).

Example 10: Standardization of *Citrus aurantifolia* Extracts

The various extracts of *Citrus aurantifolia* were standardized to Limonin by analytical HPLC method and the results were summarized in Table 2.

TABLE 2

| S. No. | Extract code | Solvent for extraction | Weight of the product | Limonin (HPLC) |
|---|---|---|---|---|
| 1 | C.A-1 | 50% ethanol | 21 g | 0.57% |
| 2 | C.A-2 | Ethanol | 9.5 g | 1.18% |
| 3 | C.A-3 | water | 21 g | 0.28% |
| 4 | C.A-4 | 50% methanol | 30 g | 0.69% |
| 5 | C.A-5 | n-butanol | 7 g | 1.70% |

Example 11: Preparation of Compositions of *Theobroma cacao* Water Extract (T.C-1) and *Citrus aurantifolia* Extracts (C.A-1 to C.A-5)

Composition-1 (C-1): The composition-1 was prepared by combining *Theobroma cacao* water extract (T.C-1) and *Citrus aurantifolia* 50% aqueous ethanol extract (C.A-1) in the ratio of 1:3.

Composition-2 (C-2): The composition-2 was prepared by combining *Theobroma cacao* water extract (T.C-1) and *Citrus aurantifolia* 50% aqueous ethanol extract (C.A-1) in the ratio of 1:2.

Composition-3 (C-3): The composition-3 was prepared by combining *Theobroma cacao* water extract (T.C-1) and *Citrus aurantifolia* 50% aqueous ethanol extract (C.A-1) in the ratio of 1:1.

Composition-4 (C-4): The composition-4 was prepared by combining *Theobroma cacao* water extract (T.C-1) and *Citrus aurantifolia* 50% aqueous ethanol extract (C.A-1) in the ratio of 2:1.

Composition-5 (C-5): The composition-5 was prepared by combining *Theobroma cacao* water extract (T.C-1) and *Citrus aurantifolia* 50% aqueous ethanol extract (C.A-1) in the ratio of 3:1.

Composition-6 (C-6): The composition-6 was prepared by combining *Theobroma cacao* water extract (T.C-1) and *Citrus aurantifolia* ethanol extract (C.A-2) in the ratio of 1:2.

Composition-7 (C-7): The composition-7 was prepared by combining *Theobroma cacao* water extract (T.C-1) and *Citrus aurantifolia* ethanol extract (C.A-2) in the ratio of 1:1.

Composition-8 (C-8): The composition-8 was prepared by combining *Theobroma cacao* water extract (T.C-1) and *Citrus aurantifolia* ethanol extract (C.A-2) in the ratio of 2:1.

Composition-9 (C-9): The composition-9 was prepared by combining *Theobroma cacao* water extract (T.C-1) and *Citrus aurantifolia* water extract (C.A-3) in the ratio of 1:3.

Composition-10 (C-10): The composition-10 was prepared by combining *Theobroma cacao* water extract (T.C-1) and *Citrus aurantifolia* water extract (C.A-3) in the ratio of 1:2.

Composition-11 (C-11): The composition-11 was prepared by combining *Theobroma cacao* water extract (T.C-1) and *Citrus aurantifolia* water extract (C.A-3) in the ratio of 1:1.

Composition-12 (C-12): The composition-12 was prepared by combining *Theobroma cacao* water extract (T.C-1) and *Citrus aurantifolia* water extract (C.A-3) in the ratio of 2:1.

Composition-13 (C-13): The composition-13 was prepared by combining *Theobroma cacao* water extract (T.C-1) and *Citrus aurantifolia* water extract (C.A-3) in the ratio of 3:1.

Composition-14 (C-14): The composition-14 was prepared by combining *Theobroma cacao* water extract (T.C-1) and *Citrus aurantifolia* 50% aqueous methanol extract (C.A-4) in the ratio of 1:2.

Composition-15 (C-15): The composition-15 was prepared by combining *Theobroma cacao* water extract (T.C-1) and *Citrus aurantifolia* 50% aqueous methanol extract (C.A-4) in the ratio of 1:1.

Composition-16 (C-16): The composition-16 was prepared by combining *Theobroma cacao* water extract (T.C-1) and *Citrus aurantifolia* 50% aqueous methanol extract (C.A-4) in the ratio of 2:1.

Composition-17 (C-17): The composition-17 was prepared by combining *Theobroma cacao* water extract (T.C-1) and *Citrus aurantifolia* butanol extract (C.A-5) in the ratio of 1:2.

Composition-18 (C-18): The composition-18 was prepared by combining *Theobroma cacao* water extract (T.C-1) and *Citrus aurantifolia* butanol extract (C.A-5) in the ratio of 1:1.

Composition-19 (C-19): The composition-19 was prepared by combining *Theobroma cacao* water extract (T.C-1) and *Citrus aurantifolia* butanol extract (C.A-5) in the ratio of 2:1.

Example 12: Preparation of Compositions of *Theobroma cacao* 50% Aqueous Ethanol Extract (T.C-2) and *Citrus aurantifolia* Extracts (C.A-1 to C.A-5)

Composition-20 (C-20): The composition-20 was prepared by combining *Theobroma cacao* 50% aqueous ethanol extract (T.C-2) and *Citrus aurantifolia* 50% aqueous ethanol extract (C.A-1) in the ratio of 1:3.

Composition-21 (C-21): The composition-21 was prepared by combining *Theobroma cacao* 50% aqueous ethanol extract (T.C-2) and *Citrus aurantifolia* 50% aqueous ethanol extract (C.A-1) in the ratio of 1:2.

Composition-22 (C-22): The composition-22 was prepared by combining *Theobroma cacao* 50% aqueous ethanol extract (T.C-2) and *Citrus aurantifolia* 50% aqueous ethanol extract (C.A-1) in the ratio of 1:1.

Composition-23 (C-23): The composition-23 was prepared by combining *Theobroma cacao* 50% aqueous ethanol extract (T.C-2) and *Citrus aurantifolia* 50% aqueous ethanol extract (C.A-1) in the ratio of 2:1.

Composition-24 (C-24): The composition-24 was prepared by combining *Theobroma cacao* 50% aqueous ethanol extract (T.C-2) and *Citrus aurantifolia* 50% aqueous ethanol extract (C.A-1) in the ratio of 3:1.

Composition-25 (C-25): The composition-25 was prepared by combining *Theobroma cacao* 50% aqueous ethanol extract (T.C-2) and *Citrus aurantifolia* ethanol extract (C.A-2) in the ratio of 1:2.

Composition-26 (C-26): The composition-26 was prepared by combining *Theobroma cacao* 50% aqueous ethanol extract (T.C-2) and *Citrus aurantifolia* ethanol extract (C.A-2) in the ratio of 1:1.

Composition-27 (C-27): The composition-27 was prepared by combining *Theobroma cacao* 50% aqueous ethanol extract (T.C-2) and *Citrus aurantifolia* ethanol extract (C.A-2) in the ratio of 2:1.

Composition-28 (C-28): The composition-28 was prepared by combining *Theobroma cacao* 50% aqueous ethanol extract (T.C-2) and *Citrus aurantifolia* water extract (C.A-3) in the ratio of 1:3.
Composition-29 (C-29): The composition-29 was prepared by combining *Theobroma cacao* 50% aqueous ethanol extract (T.C-2) and *Citrus aurantifolia* water extract (C.A-3) in the ratio of 1:2.
Composition-30 (C-30): The composition-30 was prepared by combining *Theobroma cacao* 50% aqueous ethanol extract (T.C-2) and *Citrus aurantifolia* water extract (C.A-3) in the ratio of 1:1.
Composition-31 (C-31): The composition-31 was prepared by combining *Theobroma cacao* 50% aqueous ethanol extract (T.C-2) and *Citrus aurantifolia* water extract (C.A-3) in the ratio of 2:1.
Composition-32 (C-32): The composition-32 was prepared by combining *Theobroma cacao* 50% aqueous ethanol extract (T.C-2) and *Citrus aurantifolia* water extract (C.A-3) in the ratio of 3:1.
Composition-33 (C-33): The composition-33 was prepared by combining *Theobroma cacao* 50% aqueous ethanol extract (T.C-2) and *Citrus aurantifolia* 50% aqueous methanol extract (C.A-4) in the ratio of 1:2.
Composition-34 (C-34): The composition-34 was prepared by combining *Theobroma cacao* 50% aqueous ethanol extract (T.C-2) and *Citrus aurantifolia* 50% aqueous methanol extract (C.A-4) in the ratio of 1:1.
Composition-35 (C-35): The composition-33 was prepared by combining *Theobroma cacao* 50% aqueous ethanol extract (T.C-2) and *Citrus aurantifolia* 50% aqueous methanol extract (C.A-4) in the ratio of 2:1.
Composition-36 (C-36): The composition-36 was prepared by combining *Theobroma cacao* 50% aqueous ethanol extract (T.C-2) and *Citrus aurantifolia* butanol extract (C.A-5) in the ratio of 1:2.
Composition-37 (C-37): The composition-37 was prepared by combining *Theobroma cacao* 50% aqueous ethanol extract (T.C-2) and *Citrus aurantifolia* butanol extract (C.A-5) in the ratio of 1:1.
Composition-38 (C-38): The composition-38 was prepared by combining *Theobroma cacao* 50% aqueous ethanol extract (T.C-2) and *Citrus aurantifolia* butanol extract (C.A-5) in the ratio of 2:1.

Example 13: Preparation of Compositions of *Theobroma cacao* Extracts (T.C-3, T.C-4 & T.C-5) and *Citrus aurantifolia* Extracts (C.A-1 to C.A-5)

Composition-39 (C-39): The composition-39 was prepared by combining *Theobroma cacao* ethanol extract (T.C-3) and *Citrus aurantifolia* 50% aqueous ethanol extract (C.A-1) in the ratio of 1:2.
Composition-40 (C-40): The composition-40 was prepared by combining *Theobroma cacao* ethanol extract (T.C-3) and *Citrus aurantifolia* 50% aqueous ethanol extract (C.A-1) in the ratio of 1:1.
Composition-41 (C-41): The composition-41 was prepared by combining *Theobroma cacao* ethanol extract (T.C-3) and *Citrus aurantifolia* 50% aqueous ethanol extract (C.A-1) in the ratio of 2:1.
Composition-42 (C-42): The composition-42 was prepared by combining *Theobroma cacao* ethanol extract (T.C-3) and *Citrus aurantifolia* ethanol extract (C.A-2) in the ratio of 1:2.
Composition-43 (C-43): The composition-43 was prepared by combining *Theobroma cacao* ethanol extract (T.C-3) and *Citrus aurantifolia* ethanol extract (C.A-2) in the ratio of 1:1.
Composition-44 (C-44): The composition-44 was prepared by combining *Theobroma cacao* ethanol extract (T.C-3) and *Citrus aurantifolia* ethanol extract (C.A-2) in the ratio of 2:1.
Composition-45 (C-45): The composition-45 was prepared by combining *Theobroma cacao* ethanol extract (T.C-3) and *Citrus aurantifolia* water extract (C.A-3) in the ratio of 1:2.
Composition-46 (C-46): The composition-46 was prepared by combining *Theobroma cacao* ethanol extract (T.C-3) and *Citrus aurantifolia* water extract (C.A-3) in the ratio of 1:1.
Composition-47 (C-47): The composition-47 was prepared by combining *Theobroma cacao* ethanol extract (T.C-3) and *Citrus aurantifolia* water extract (C.A-3) in the ratio of 2:1.
Composition-48 (C-48): The composition-48 was prepared by combining *Theobroma cacao* ethanol extract (T.C-3) and *Citrus aurantifolia* 50% aqueous methanol extract (C.A-4) in the ratio of 1:2.
Composition-49 (C-49): The composition-49 was prepared by combining *Theobroma cacao* ethanol extract (T.C-3) and *Citrus aurantifolia* 50% aqueous methanol extract (C.A-4) in the ratio of 1:1.
Composition-50 (C-50): The composition-50 was prepared by combining *Theobroma cacao* ethanol extract (T.C-3) and *Citrus aurantifolia* 50% aqueous methanol extract (C.A-4) in the ratio of 2:1.
Composition-51 (C-51): The composition-51 was prepared by combining *Theobroma cacao* ethanol extract (T.C-3) and *Citrus aurantifolia* butanol extract (C.A-5) in the ratio of 1:2.
Composition-52 (C-52): The composition-52 was prepared by combining *Theobroma cacao* ethanol extract (T.C-3) and *Citrus aurantifolia* butanol extract (C.A-5) in the ratio of 1:1.
Composition-53 (C-53): The composition-53 was prepared by combining *Theobroma cacao* ethanol extract (T.C-3) and *Citrus aurantifolia* butanol extract (C.A-5) in the ratio of 2:1.
Composition-54 (C-54): The composition-54 was prepared by combining *Theobroma cacao* 50% methanol extract (T.C-4) and *Citrus aurantifolia* water extract (C.A-3) in the ratio of 1:2.
Composition-55 (C-55): The composition-55 was prepared by combining *Theobroma cacao* 50% methanol extract (T.C-4) and *Citrus aurantifolia* water extract (C.A-3) in the ratio of 1:1.
Composition-56 (C-56): The composition-56 was prepared by combining *Theobroma cacao* 50% methanol extract (T.C-4) and *Citrus aurantifolia* water extract (C.A-3) in the ratio of 2:1.
Composition-57 (C-57): The composition-57 was prepared by combining *Theobroma cacao* 50% methanol extract (T.C-4) and *Citrus aurantifolia* 50% ethanol extract (C.A-1) in the ratio of 1:2.
Composition-58 (C-58): The composition-58 was prepared by combining *Theobroma cacao* 50% methanol extract (T.C-4) and *Citrus aurantifolia* 50% ethanol extract (C.A-1) in the ratio of 1:1.
Composition-59 (C-59): The composition-59 was prepared by combining *Theobroma cacao* 50% methanol extract (T.C-4) and *Citrus aurantifolia* 50% ethanol extract (C.A-1) in the ratio of 2:1.

Composition-60 (C-60): The composition-60 was prepared by combining *Theobroma cacao* butanol extract (T.C-5) and *Citrus aurantifolia* water extract (C.A-3) in the ratio of 1:2.

Composition-61 (C-61): The composition-61 was prepared by combining *Theobroma cacao* butanol extract (T.C-5) and *Citrus aurantifolia* water extract (C.A-3) in the ratio of 1:1.

Composition-62 (C-62): The composition-62 was prepared by combining *Theobroma cacao* butanol extract (T.C-5) and *Citrus aurantifolia* water extract (C.A-3) in the ratio of 2:1.

Composition-63 (C-63): The composition-63 was prepared by combining *Theobroma cacao* butanol extract (T.C-5) and *Citrus aurantifolia* 50% ethanol extract (C.A-1) in the ratio of 1:2.

Composition-64 (C-64): The composition-64 was prepared by combining *Theobroma cacao* butanol extract (T.C-5) and *Citrus aurantifolia* 50% ethanol extract (C.A-1) in the ratio of 1:1.

Composition-65 (C-65): The composition-65 was prepared by combining *Theobroma cacao* butanol extract (T.C-5) and *Citrus aurantifolia* 50% ethanol extract (C.A-1) in the ratio of 2:1.

Example 14: Formulation of the Compositions

Composition-66 (C-66): The composition-66 was prepared by combining 60 g of *Theobroma cacao* water extract (T.C-1), 30 g of *Citrus aurantifolia* 50% aqueous ethanol extract (C.A-1), 9 g of maltodextrin and 1 g of syloid.

Composition-67 (C-67): The composition-67 was prepared by combining 53.33 g of *Theobroma cacao* water extract (T.C-1), 26.67 g of *Citrus aurantifolia* 50% aqueous ethanol extract (C.A-1), 18 g of maltodextrin and 2 g of syloid in presence of ethanol/water and dried to give the composition.

Composition-68 (C-68): The composition-68 was prepared by combining 53.2 g of *Theobroma cacao* water extract (T.C-1), 26.6 g of *Citrus aurantifolia* 50% aqueous ethanol extract (C.A-1), 18.2 g of glucidex-12D and 2 g of syloid in presence of ethanol/water and dried to give the composition.

Example 15: General Procedure for Adipogenesis Inhibition Assay

Mouse 3T3-L1 pre-adipocytes (50000 cells/well in 500 µL) were seeded in a 48-well cell culture plate and maintained in DMEM medium containing 10% FBS at 37° C. in a humidified atmosphere of 5% $CO_2$. After the cells were confluent (~2 days), the cells were treated with different concentrations of the test samples in differentiation medium (DM) containing 0.5 mM 3-isobutyl-1-methylxanthine (IBMX), 1 µM dexamethasone, and 500 nM insulin in DMEM with 10% FBS for 48 hours. The cell culture medium was changed to post-DM containing 100 nM insulin in DMEM with 10% FBS with respective concentrations of test samples, and post-DM along with respective concentrations of test samples was freshly replaced every 48 hours until day 6. The cells were subjected to Oil red O staining, 8 days after the initiation of differentiation.

Oil Red O Staining: The medium was aspirated and 0.5 mL of 10% formaldehyde was added to each well and incubated for 2 hours at room temperature. Formaldehyde was removed from the wells and 0.25 mL of 60% isopropanol was added and the plate was allowed to dry completely. One hundred microliters of red oil O was added and incubated for 20 minutes in dark at room temperature. Red oil O was aspirated and the plate was washed 4 times with distilled water. The plate was dried completely and 150 µL of 100% isopropanol was added, mixed thoroughly and 75 µL was transferred to a 96-well assay plate and the absorbance was measured at 550 nm in Spectramax5e plate reader. Percent inhibition of adipogenesis was calculated using the formula below:

$$\% \text{ inhibition of adipogenesis} = \frac{\text{Average } OD \text{ of Vehicle Control} - \text{Average } OD \text{ of Treatments}}{\text{Average } OD \text{ of Vehicle Control}} \times 100$$

With the above procedure, all the compositions are screened for their adipogenesis inhibition and the results were presented in tables 3, 4 & 5.

TABLE 3

Adipogenesis activity of the compositions containing *Theobroma cacao* extract (T.C-1) and *Citrus aurantifolia* extracts (C.A-1 to C.A-5).

| Comp # | T.C-1 µg/mL | T.C-1 % inhibition | C.A-1 µg/mL | C.A-1 % inhibition | Ratio | Comp Dose µg/mL | % Inhibition of Adipogenesis Additive (Calculated) | % Inhibition of Adipogenesis Observed |
|---|---|---|---|---|---|---|---|---|
| C-1 | 1.25 | 11.40 | 3.75 | 21.93 | 1:3 | 5 | 33.33 | 40.26 |
| C-2 | 1.67 | 15.23 | 3.33 | 19.47 | 1:2 | 5 | 34.7 | 44.78 |
| C-3 | 2.5 | 22.80 | 2.5 | 14.62 | 1:1 | 5 | 37.42 | 49.32 |
| C-4 | 3.33 | 30.37 | 1.67 | 9.76 | 2:1 | 5 | 40.13 | 53.42 |
| C-5 | 3.75 | 34.20 | 1.25 | 7.31 | 3:1 | 5 | 41.51 | 51.13 |
| | T.C-1 | | C.A-2 | | | | | |
| C-6 | 1.67 | 11.40 | 3.33 | 6.86 | 1:2 | 5 | 18.26 | 34.25 |
| C-7 | 2.5 | 17.06 | 2.5 | 5.15 | 1:1 | 5 | 22.21 | 31.94 |
| C-8 | 3.33 | 22.72 | 1.67 | 3.44 | 2:1 | 5 | 26.16 | 48.61 |
| | T.C-1 | | C.A-3 | | | | | |
| C-10 | 1.67 | 16.53 | 3.33 | 29.62 | 1:2 | 5 | 46.15 | 59.24 |
| C-12 | 3.33 | 32.97 | 1.67 | 14.86 | 2:1 | 5 | 47.83 | 62.56 |
| | T.C-1 | | C.A-4 | | | | | |
| C-14 | 1.67 | 12.81 | 3.33 | 1.66 | 1:2 | 5 | 14.47 | 24.62 |
| C-15 | 2.5 | 19.18 | 2.5 | 1.24 | 1:1 | 5 | 20.42 | 38.88 |

TABLE 3-continued

Adipogenesis activity of the compositions containing *Theobroma cacao* extract (T.C-1) and *Citrus aurantifolia* extracts (C.A-1 to C.A-5).

| Comp # | T.C-1 µg/mL | % inhibition | C.A-1 µg/mL | % inhibition | Ratio | Comp Dose µg/mL | % Inhibition of Adipogenesis Additive (Calculated) | Observed |
|---|---|---|---|---|---|---|---|---|
| | T.C-1 | | C.A-5 | | | | | |
| C-17 | 0.83 | 7.52 | 1.67 | 8.20 | 1:2 | 2.5 | 15.72 | 28.97 |
| C-18 | 1.25 | 11.33 | 1.25 | 6.14 | 1:1 | 2.5 | 17.47 | 22.54 |

TABLE 4

Adipogenesis activity of the compositions containing *Theobroma cacao* extract (T.C-2) and *Citrus aurantifolia* extracts (C.A-1 to C.A-4).

| Comp # | T.C-2 µg/mL | % inhibition | C.A-1 µg/mL | % inhibition | Ratio | Comp Dose µg/mL | % Inhibition of Adipogenesis Additive (Calculated) | Observed |
|---|---|---|---|---|---|---|---|---|
| C-20 | 0.63 | 1.57 | 1.87 | 29.63 | 1:3 | 2.5 | 31.2 | 45.58 |
| C-21 | 0.83 | 2.07 | 1.67 | 26.46 | 1:2 | 2.5 | 28.53 | 40.19 |
| C-22 | 1.25 | 3.12 | 1.25 | 19.81 | 1:1 | 2.5 | 22.93 | 38.46 |
| C-23 | 1.67 | 4.17 | 0.83 | 13.15 | 2:1 | 2.5 | 17.32 | 28.74 |
| C-24 | 1.87 | 4.67 | 0.63 | 9.98 | 3:1 | 2.5 | 14.65 | 21.71 |
| | T.C-2 | | C.A-2 | | | | | |
| C-25 | 0.83 | 3.09 | 1.67 | 5.34 | 1:2 | 2.5 | 8.43 | 15.34 |
| C-26 | 1.25 | 4.65 | 1.25 | 3.99 | 1:1 | 2.5 | 8.65 | 27.00 |
| C-27 | 1.67 | 6.22 | 0.83 | 2.65 | 2:1 | 2.5 | 8.87 | 11.02 |
| | T.C-2 | | C.A-3 | | | | | |
| C-29 | 1.67 | 2.80 | 3.33 | 20.66 | 1:2 | 5 | 23.46 | 35.05 |
| C-31 | 3.33 | 5.76 | 1.67 | 10.30 | 2:1 | 5 | 16.06 | 24.80 |
| | T.C-2 | | C.A-4 | | | | | |
| C-33 | 3.33 | 5.96 | 6.67 | 5.05 | 1:2 | 10 | 11.01 | 21.50 |
| C-34 | 1.25 | 2.41 | 1.25 | 0.5 | 1:1 | 2.5 | 2.91 | 23.80 |
| C-35 | 3.33 | 8.93 | 1.67 | 4.48 | 2:1 | 5 | 13.41 | 19.37 |

TABLE 5

Adipogenesis activity of the compositions containing *Theobroma cacao* extracts (T.C-3, T.C-4, T.C-5) and *Citrus aurantifolia* extracts (C.A-1 to C.A-5).

| Comp # | T.C-3 µg/mL | % inhibition | C.A-1 µg/mL | % inhibition | Ratio | Comp Dose µg/mL | % Inhibition of Adipogenesis Additive (Calculated) | Observed |
|---|---|---|---|---|---|---|---|---|
| C-39 | 0.83 | 4.43 | 1.67 | 15.02 | 1:2 | 2.5 | 19.45 | 27.20 |
| C-40 | 1.25 | 6.67 | 1.25 | 11.24 | 1:1 | 2.5 | 17.91 | 22.31 |
| C-41 | 1.67 | 8.91 | 0.83 | 7.46 | 2:1 | 2.5 | 16.37 | 20.66 |
| | T.C-3 | | C.A-2 | | | | | |
| C-43 | 5.0 | 6.78 | 5.0 | 8.76 | 1:1 | 10 | 15.54 | 37.33 |
| | T.C-3 | | C.A-3 | | | | | |
| C-45 | 0.83 | 7.23 | 1.67 | 18.21 | 1:2 | 2.5 | 25.44 | 31.24 |
| C-47 | 1.67 | 14.54 | 0.83 | 9.05 | 2:1 | 2.5 | 23.59 | 26.00 |
| | T.C-3 | | C.A-4 | | | | | |
| C-49 | 2.5 | 3.48 | 2.5 | 6.22 | 1:1 | 5 | 9.7 | 15.17 |
| | T.C-3 | | C.A-5 | | | | | |
| C-51 | 0.83 | 0.86 | 1.67 | 5.97 | 1:2 | 2.5 | 6.83 | 17.86 |
| C-52 | 1.25 | 1.29 | 1.25 | 4.47 | 1:1 | 2.5 | 5.76 | 16.95 |

TABLE 5-continued

Adipogenesis activity of the compositions containing *Theobroma cacao* extracts (T.C-3, T.C-4, T.C-5) and *Citrus aurantifolia* extracts (C.A-1 to C.A-5).

| Comp # | T.C-3 µg/mL | % inhibition | C.A-1 µg/mL | % inhibition | Ratio | Comp Dose µg/mL | % Inhibition of Adipogenesis Additive (Calculated) | Observed |
|---|---|---|---|---|---|---|---|---|
| | T.C-4 | | C.A-1 | | | | | |
| C-59 | 1.67 | 7.10 | 0.83 | 8.54 | 2:1 | 2.5 | 15.64 | 19.22 |
| | T.C-5 | | C.A-3 | | | | | |
| C-60 | 0.83 | 10.42 | 1.67 | 23.28 | 1:2 | 2.5 | 33.7 | 44.05 |
| | T.C-5 | | C.A-1 | | | | | |
| C-64 | 1.25 | 2.58 | 1.25 | 15.38 | 1:1 | 2.5 | 17.96 | 22.95 |

Example 16: General Procedure for Increase of Adipolysis Assay

Mouse 3T3-L1 preadipocytes (50000 cells/well in 500 µL) were seeded in a 48-well cell culture plate and maintained in DMEM containing 10% FBS at 37° C. in a humidified atmosphere of 5% $CO_2$. After the cells were confluent (~2 days), the differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed with 600 µL of DMEM without phenol red. Cells were treated with different concentrations of test samples (50 µL) in phenol red-free DMEM medium containing 2% BSA (50 µL) and incubated for 4 hours at 37° C. in a $CO_2$ incubator. After incubation, 25 µL of cell-free supernatants were collected from the wells into a 96-well assay plate and processed for glycerol assay.

Glycerol assay: Twenty five microliters of standards or samples were added to 100 µL of glycerol reagent [ATP: 20.65 mg, $MgCl_2$: 46.20 mg, N-Ethyl-N-(3-Sulfopropyl)-m-ansidine sodiumsalt: 31.10 mg, Aminoantipyrol: 1.90 mg, Glycerol Kinase: 10.2 µL, Glycerol Oxidase: 125 µL, HRP: 62.5 µL were dissolved in 50 mL of 1×PBS] in a 96-well assay plate and incubated for 15 minutes at room temperature. Absorbance was measured at 550 nm in Spectramax5e plate reader. A 7-point Glycerol standard curve was generated in the range of 0.781-50 µg/mL. Percent increase in lipolysis was estimated using the formula below:

$$\% \text{ increase in glycerol content in the test samples} = \frac{\text{Glycerol conc. in sample} - \text{Glycerol conc. in vehicle control}}{\text{Glycerol conc. in vehicle control}} \times 100$$

With the above procedure, all the compositions are screened for their adipolysis increase and the results were presented in tables 6 & 7.

TABLE 6

Adipolysis activity of the compositions containing *Theobroma cacao* extract (T.C-1) and *Citrus aurantifolia* extracts (C.A-1 to C.A-4).

| Comp # | T.C-1 µg/mL | % increase | C.A-1 µg/mL | % increase | Ratio | Comp Dose µg/mL | % Increase of Adipolysis Additive (Calculated) | Observed |
|---|---|---|---|---|---|---|---|---|
| C-1 | 5.0 | 22.13 | 15.0 | 8.02 | 1:3 | 20 | 30.15 | 34.28 |
| C-2 | 6.67 | 29.52 | 13.33 | 7.12 | 1:2 | 20 | 36.64 | 47.88 |
| C-3 | 10.0 | 44.25 | 10.0 | 5.34 | 1:1 | 20 | 49.59 | 56.69 |
| C-4 | 3.33 | 14.43 | 1.67 | 2.76 | 2:1 | 5 | 17.19 | 25.18 |
| C-5 | 3.75 | 15.13 | 1.25 | 2.07 | 3:1 | 5 | 17.2 | 26.11 |
| | T.C-1 | | C.A-2 | | | | | |
| C-7 | 5.0 | 17.69 | 5.0 | 5.77 | 1:1 | 10 | 23.46 | 32.05 |
| | T.C-1 | | C.A-3 | | | | | |
| C-9 | 2.5 | 5.01 | 7.5 | 4.21 | 1:3 | 10 | 9.22 | 32.35 |
| C-10 | 6.67 | 14.80 | 13.33 | 13.19 | 1:2 | 20 | 27.99 | 31.93 |
| C-11 | 5.0 | 10.02 | 5.0 | 2.80 | 1:1 | 10 | 12.82 | 24.06 |
| C-12 | 6.67 | 13.37 | 3.33 | 1.86 | 2:1 | 10 | 15.23 | 24.78 |
| C-13 | 7.5 | 15.03 | 2.5 | 1.40 | 3:1 | 10 | 16.43 | 28.34 |
| | T.C-1 | | C.A-4 | | | | | |
| C-15 | 5.0 | 8.48 | 5.0 | 5.58 | 1:1 | 10 | 14.06 | 27.68 |

TABLE 7

Adipolysis activity of the compositions containing *Theobroma cacao* extract (T.C-2 and T.C-3) and *Citrus aurantifolia* extracts (C.A-1 and C.A-5).

| Comp # | T.C-2 μg/mL | % increase | C.A-1 μg/mL | % increase | Ratio | Comp Dose μg/mL | % Increase of Adipolysis Additive (Calculated) | Observed |
|---|---|---|---|---|---|---|---|---|
| C-20 | 1.25 | 3.02 | 3.75 | 0.52 | 1:3 | 5 | 3.54 | 12.26 |
| C-21 | 1.67 | 4.04 | 3.33 | 0.46 | 1:2 | 5 | 4.50 | 16.58 |
| C-22 | 2.5 | 6.04 | 2.5 | 0.34 | 1:1 | 5 | 6.38 | 31.26 |
| C-23 | 3.33 | 8.05 | 1.67 | 0.23 | 2:1 | 5 | 8.28 | 16.27 |
| C-24 | 3.75 | 9.07 | 1.25 | 0.17 | 3:1 | 5 | 9.24 | 16.23 |
| | T.C-3 | | C.A-5 | | | | | |
| C-52 | 10.0 | 6.31 | 10.0 | 8.05 | 1:1 | 20 | 14.36 | 23.95 |

Example 17: General Procedure for FGF21 Assay

Mouse 3T3-L1 pre-adipocytes (150000 cells/well in 3 mL) were seeded in a 6-well cell culture plate and maintained in DMEM medium containing 10% FBS and 4.5 g/L glucose at 37° C. in a humidified atmosphere of 5% $CO_2$. After the cells were confluent (~2 days), differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed twice with DMEM medium containing 1% FBS. Cells were treated with different concentrations of test samples (50 µL) in DMEM medium containing 1% FBS (1 mL total volume) and incubated for another 48 hours at 37° C. in a $CO_2$ incubator. After incubation, 50 µL of cell-free supernatants were collected from the wells and processed for FGF21 analysis by ELISA. FGF21 ELISA (R&D Systems Cat #DY2539) was performed according to the manufacturer's protocol.

Percent increase in FGF21 was calculated using the formula below:

$$\% \text{ Increase of } FGF21 = \frac{FGF21 \text{ Concn. in Treatment} - FGF21 \text{ Concn. in Vehicle Control}}{FGF21 \text{ Concn. in Vehicle Control}} \times 100$$

With the above procedure, the selected compositions were screened for their FGF-21 increase over control and the results were summarized in table 8.

TABLE 8

FGF 21 activity of the compositions containing *Theobroma cacao* extracts and *Citrus aurantifolia* extracts.

| Comp # | T.C-1 μg/mL | % Increase | C.A-1 μg/mL | % Increase | Ratio | Comp Dose μg/mL | % Increase of FGF 21 Additive (Calculated) | Observed |
|---|---|---|---|---|---|---|---|---|
| C-1 | 1.25 | 7.54 | 3.75 | 20.95 | 1:3 | 5 | 28.49 | 56.36 |
| C-2 | 1.67 | 10.08 | 3.33 | 18.60 | 1:2 | 5 | 28.68 | 44.21 |
| C-3 | 12.5 | 12.10 | 12.5 | 17.96 | 1:1 | 25 | 30.05 | 42.94 |
| C-4 | 3.33 | 20.09 | 1.67 | 9.33 | 2:1 | 5 | 29.42 | 41.47 |
| C-5 | 3.75 | 22.63 | 1.25 | 6.98 | 3:1 | 5 | 29.61 | 40.40 |
| | T.C-1 | | C.A-3 | | | | | |
| C-10 | 8.33 | 26.01 | 16.67 | 55.83 | 1:2 | 25 | 81.84 | 90.58 |
| | T.C-1 | | C.A-4 | | | | | |
| C-15 | 12.5 | 31.18 | 12.5 | 16.06 | 1:1 | 25 | 47.24 | 56.41 |
| | T.C-2 | | C.A-1 | | | | | |
| C-20 | 1.67 | 1.80 | 3.33 | 17.00 | 1:2 | 5 | 18.8 | 25.78 |
| C-21 | 2.5 | 2.7 | 2.5 | 12.77 | 1:1 | 5 | 15.47 | 23.60 |
| C-22 | 3.33 | 3.60 | 1.67 | 8.53 | 2:1 | 5 | 12.13 | 22.30 |
| | T.C-2 | | C.A-5 | | | | | |
| C-36 | 1.67 | 2.67 | 3.33 | 11.79 | 1:2 | 5 | 14.46 | 61.60 |
| C-37 | 2.5 | 3.99 | 2.5 | 8.86 | 1:1 | 5 | 12.85 | 59.10 |
| C-38 | 3.33 | 5.31 | 1.67 | 5.92 | 2:1 | 5 | 11.23 | 42.39 |

Example 18: General Procedure for UCP-1 Assay

Mouse 3T3-L1 pre-adipocytes (150000 cells/well in 3 mL) were seeded in a 6-well cell culture plate and maintained in DMEM medium containing 10% FBS and 4.5 g/L glucose at 37° C. in a humidified atmosphere of 5% $CO_2$. After the cells were confluent (~2 days), differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed twice with DMEM medium containing 1% FBS. Cells were treated with different concentrations of test samples (50 µL) in DMEM medium containing 1% FBS (1 mL total volume) and incubated for another 48 hours at 37° C. in a $CO_2$ incubator.

Western Blot:

After the incubation, cell culture plates were placed on ice tray and washed twice with 1×PBS. Eighty microliters of lysis buffer (10 mM Tris-HCl pH 7.4, 150 mM NaCl, 1 mM EDTA, 1 mM PMSF, 10 µg/mL Aprotinin, 10 µg/mL Leupeptin, 1% Triton X-100, 1 mM NaF, 1 mM $Na_3VO_4$, 0.5% Sodium deoxycholate, and 1 µM Pepstatin) was added to each well and the cell lysates were collected in respective microfuge tubes. The microfuge tubes were sonicated for 1 min. and cellular protein was collected after centrifugation at 21952×g. Protein was quantified using Pierce BCA protein assay kit (Thermo Scientific Cat #23225). SDS-PAGE was performed for the protein samples and resolved proteins were transferred onto nitrocellulose membrane using wet blotting method. Briefly, 10 µg of protein was loaded onto acrylamide gel (10% resolving) and ran at 100V for approximately 1 hr 40 min. At the end of the run, proteins were transferred to the nitrocellulose membrane by placing transfer system at 4° C. chamber (100V for 2 hrs). After the transfer, UCP-1 was probed using anti-UCP-1 antibody (Thermo Scientific Cat #PA1-24894; 1:10000 dilution) incubating at 4° C. for 18 hrs. β-Actin was probed using anti-β-actin antibody (Sigma Cat #A4700-100 uL; 1:10000 dilution) incubating at room temperature for 2 hrs. Peroxidase affinipure mouse anti-goat secondary antibody (Jackson Immuno Research Cat #205-035-108; 1:10000 dilution) was added and incubated for 30 mins. at room temperature. Finally, the blots were developed using a chemiluminiscent substrate (Thermo Scientific Cat #34080) and images were captured using Bio-Rad Molecular imager (Model: ChemiDOC XRS+). The intensities of the UCP-1 protein bands were calculated using Carestream MI software and normalized using β-Actin to obtain Relative indices. The percent UCP-1 expression over control was calculated using the following formula:

$$\%UCP\text{-}1 \text{ expression over control} = \frac{\text{Relative } UCP\text{-}1 \text{ expression in Test samples} - \text{Relative } UCP\text{-}1 \text{ expression in Control}}{\text{Relative } UCP\text{-}1 \text{ expression in Test samples}} \times 100$$

With the above procedure, the selected compositions were screened for their % UCP-1 expression over control and the results are presented in table 9.

TABLE 9

UCP-1 expression of the compositions of *Theobroma cacao* extracts and *Citrus aurantifolia* extracts.

| Compo# | Ratio | Dose µg/mL | Control | Relative index of UCP-1 expression (Arbitrary units) | % UCP-1 expression over control |
|---|---|---|---|---|---|
| C-1 | 1:3 | 25 | 0.415 | 0.673 | 38.48 |
| C-2 | 1:2 | 25 | | 0.631 | 34.23 |
| C-3 | 1:1 | 25 | | 0.627 | 33.81 |
| C-4 | 2:1 | 25 | | 0.599 | 30.71 |
| C-5 | 3:1 | 25 | | 0.582 | 28.69 |
| C-58 | 1:1 | 25 | 0.618 | 0.820 | 24.63 |
| C-59 | 2:1 | 25 | | 0.702 | 11.96 |

Example 19: General Procedure for β3AR Assay

Mouse 3T3-L1 pre-adipocytes (150000 cells/well in 3 mL) were seeded in a 6-well cell culture plate and maintained in DMEM medium containing 10% FBS and 4.5 g/L glucose at 37° C. in a humidified atmosphere of 5% $CO_2$. After the cells were confluent (~2 days), differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed twice with DMEM medium containing 1% FBS. Cells were treated with different concentrations of test samples (50 µL) in DMEM medium containing 1% FBS (1 mL total volume) and incubated for another 48 hours at 37° C. in a $CO_2$ incubator.

Western Blot:

After the incubation, cell culture plates were placed on ice tray and washed twice with 1×PBS. Eighty microliters of lysis buffer (10 mM Tris-HCl pH 7.4, 150 mM NaCl, 1 mM EDTA, 1 mM PMSF, 10 µg/mL Aprotinin, 10 µg/mL Leupeptin, 1% Triton X-100, 1 mM NaF, 1 mM $Na_3VO_4$, 0.5% Sodium deoxycholate, and 1 µM Pepstatin) was added to each well and the cell lysates were collected in respective microfuge tubes. The microfuge tubes were sonicated for 1 min. and cellular protein was collected after centrifugation at 21952×g. Protein was quantified using Pierce BCA protein assay kit (Thermo Scientific Cat #23225). SDS-PAGE was performed for the protein samples and resolved proteins were transferred onto nitrocellulose membrane using wet blotting method. Briefly, 10 µg of protein was loaded onto acrylamide gel (10% resolving) and ran at 100V for approximately 1 hr 40 min. At the end of the run, proteins were transferred to the nitrocellulose membrane by placing transfer system at 4° C. chamber (100V for 2 hrs). After the transfer, β3AR was probed using anti-β3AR antibody (Biorbyt Cat #orb221343; 1:500 dilution) incubating at 4° C. for 18 hrs. β-Actin was probed using anti-β-actin antibody (Sigma Cat #A4700-100 uL; 1:10000 dilution) incubating at room temperature for 2 hrs. Peroxidase affinipure mouse anti-goat secondary antibody (Jackson Immuno Research Cat #205-035-108; 1:10000 dilution) was added and incubated for 30 mins. at room temperature. Finally, the blots were developed using a chemiluminiscent substrate (Thermo Scientific Cat #34080) and images were captured using Bio-Rad Molecular imager (Model: ChemiDOC XRS+). The intensities of the β3AR protein bands were calculated using Carestream MI software and normalized using β-Actin to obtain Relative indices. The percent β3AR expression over control was calculated using the following formula:

$$\%\beta3AR \text{ expression over control} = \frac{\text{Relative } \beta3AR \text{ expression in Test samples} - \text{Relative } \beta3AR \text{ expression in Control}}{\text{Relative } \beta3AR \text{ expression in Test samples}} \times 100$$

With the above procedure, all the compositions are screened for their β3AR expression over control and the results were presented in table 10.

TABLE 10

β3AR expression of the compositions of *Theobroma cacao* and *Citrus aurantifolia*.

| Compo# | Ratio | Dose µg/mL | Control | Relative index of β3AR expression (Arbitrary units) | % β3AR expression over control |
|---|---|---|---|---|---|
| C-1 | 1:3 | 2.5 | 0.524 | 0.821 | 36.17 |
| C-2 | 1:2 | 2.5 | | 0.838 | 37.47 |
| C-3 | 1:1 | 2.5 | | 1.070 | 51.02 |
| C-21 | 1:2 | 2.5 | | 0.645 | 18.75 |
| C-22 | 1:1 | 2.5 | | 0.600 | 12.66 |

Example 20

Figure 2:
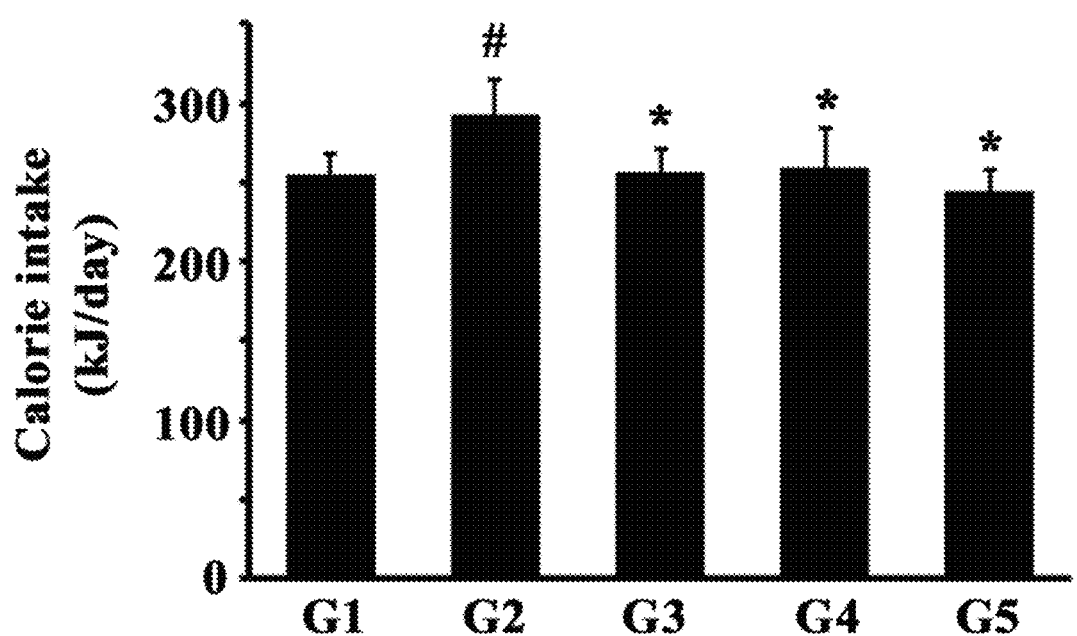
FIG. 2: Bar diagram depicts the reduction of daily dietary calorie intake by the diet induced obese rats supplemented with Composition 67. Each bar presents mean±SD. G1 and G2 represent the groups of rats supplemented with normal chow and high fat diet, respectively. G3, G4 and G5 represent high fat diet plus 100 and 300 mg/kg body weight of composition 67, and 10 mg/kg body weight of Sibutramine supplemented rats, respectively. n=7; Significant at $p<0.05$; #G1 vs. G2; *G2 vs. the treatment groups.

In-vivo Anti-obesity activity of composition-67 containing *Theobroma cacao* water extract (T.C-1) and *Citrus aurantifolia* 50% aqueous ethanol extract (C.A-1), maltodextrin and syloid in high fat diet induced obesity model of Sprague-Dawley rats.
Induction: Selected healthy Sprague-Dawley rats were randomly assigned to Normal control (N=7) or High Fat Diet groups (n=34). All the animals allocated in the high fat diet induced obesity group were made experimentally obese through dietary intervention during the first four weeks induction period by feeding high fat diet. Upon end of induction period, obese animals were randomized based on body weights in to four groups (n=7) viz. G2-Obese control, G3-Composition-67 (100 mg/Kg; p.o.), G4-Composition-67 (300 mg/Kg; p.o.) and G5-Sibutramine (10 mg/Kg; p.o.).
Treatment: Following 4 weeks of induction phase, the animals were treated orally (using oral feeding gavage) with allocated test substances or vehicle daily for 4 weeks. The animals of treatment groups were supplemented with 100 mg (G3) or 300 mg/kg (G4) body weight of Composition-67 (C-67) or 10 mg/kg body weight of Sibutramine in 10 mL of 0.5% CMC in water for 4 weeks. The control group of animals received only the vehicle (10 mL of 0.5% CMC in water) during this period. During the treatment phase, all animals were provided with the standard rodent diet till the end of the study.
Parameters evaluated: Body weight of individual animals was recorded weekly during the entire duration of the study and mean body weights were determined. The body weight gain was calculated weekly during treatment phase in comparison to the respective initial body weights at the end of treatment. The results were depicted in FIGS. 1A and 1B.
Dietary Calorie consumption: During the treatment phase of the study, the total amount of feed consumption by the experimental rats was recorded. The total amount of feed consumed in 28 days was averaged to estimate the daily feed consumption (in grams). The average feed consumption (in gram) was multiplied by the quantity of energy (kJ/gram) supplied by the regular chow (3.43 kJ/gram) and the high fat diet (5.15 kJ/gran). The daily average dietary calorie consumptions (kJ/day) by the experimental groups are presented as (FIG. 2).
Following euthanasia, the visceral (retroperitoneal, epididymal, peri-renal and mesenteric) fat tissues were collected from the rats and weighed on an electronic balance with 0.01 g sensitivity (Mettler Toledo, Columbus, Ohio). The observations on modulation in visceral fat weight are summarized in FIG. 3.
Fat tissue morphometry: The epididymal fat tissues collected from individual animals were fixed in 10% formalin. The paraffin embedded tissues were cut into 5 µm sections and the sections were processed following a standard protocol. The hematoxylin-eosin stained tissue sections were observed under a microscope at 20× (Axio Scope A1, Carl Zeiss GmbH, Jena, Germany). Pixel sizes of the fat cells were estimated and a conversion scale of 0.1694 µm per pixel was used to estimate the area of each cell. The fat cell size data is depicted in FIG. 4.
Serum biomarkers evaluation: Blood samples were collected from all the animals at the end of the study. Serum was separated from blood sample and analyzed for Leptin, triiodothyronine (T3) and thyroxine (T4) using commercial ELISA kits (Leptin ELISA kit, EMD Millipore, Billerica, Mass.; T3 and T4 ELISA kits, Calbiotech, EL Cajon, Calif.). The assays were performed following the instructions provided by the vendors. The serum leptin data for the treatment groups in comparison to the control group is summarized in FIG. V. Thyroid hormone balance (T3/T4) was calculated for all the animals and the results are summarized in FIG. 6.
Fat cell immunohistochemistry: Immunohistochemistry of UCP-1 was performed on paraffin embedded epididymal fat tissue using DAB staining method as per the kit instructions (EMD Millipore, Billerica, Mass.). The tissue sections were reacted with UCP-1 antibody (Invitrogen, Carlsbad, Calif.), followed by streptavidin-conjugated HRP. Finally, the antibody specific chromogenic reaction was developed with diaminobenzedene (DAB). The images of the UCP-1 stained tissue sections were captured using an Axio Observer.Z1 microscope (Carl-Zeiss, Oberkochen, Germany). The representative photomicrographs of the UCP-1 stained epididymal fat tissue sections are presented in FIG. 7.

We claim:
1. A synergistic herbal composition effective for at least one of promoting lipolysis, inhibiting adipogenesis, inhibiting lipid accumulation, increase of fibroblast growth factor-21 (FGF-21), increase of uncoupling protein (UCP-1) expression and increase of 33-adrenoceptors (33-ARs) in a patient in need thereof, the synergistic herbal composition comprising a combination of:
   a first ingredient, wherein the first ingredient is an extract of a *Theobroma cacao* seed, obtained by extraction with water, ethanol, methanol, n-butanol, or a mixture thereof; and
   a second ingredient, wherein the second ingredient is an extract of a *Citrus aurantifolia* fruit peel or whole fruit, obtained by extraction with water, ethanol, methanol, n-butanol, or a mixture thereof;
   wherein the first ingredient and the second ingredient are present in the synergistic herbal composition in a ratio ranging from 1:9 to 9:1 by weight.
2. The synergistic herbal composition as claimed in claim 1, wherein the first ingredient and the second ingredient are present in the synergistic herbal composition in a ratio ranging from 1:3 to 3:1 by weight.

3. The synergistic herbal composition as claimed in claim 2, wherein the synergistic herbal composition is effective for inhibiting adipogenesis in a patient in need thereof.

4. The synergistic herbal composition as claimed in claim 2, wherein the synergistic herbal composition is effective for increasing adipolysis in a patient in need thereof.

5. The synergistic herbal composition as claimed in claim 2, wherein the synergistic herbal composition is effective for increasing FGF21 activity in a patient in need thereof.

6. The synergistic herbal composition as claimed in claim 2, wherein first ingredient and the second ingredient are the only herbal ingredients in the synergistic herbal composition.

7. The synergistic composition as claimed in claim 1, optionally comprising at least one component selected from the group consisting of pharmaceutically or nutraceutically or dietetically acceptable excipients, carriers and diluents.

8. The synergistic composition as claimed in claim 7, wherein the pharmaceutically or nutraceutically or dietetically acceptable excipients, carriers and diluents are selected from the group consisting of monosaccharides, disaccharides, polycarbohydrates, dextrins, polyhydric alcohols or sugar alcohols, cellulose or cellulose derivatives, silicates, metallic stearates, organic acids, fatty acid esters, esters of poly sorbate, natural gums, vitamin B group, nicotinamide, calcium pantothenate, amino acids, proteins; inorganic metal salts, Natural pigments, flavors, Class I & Class II preservatives, mixtures thereof, and aqueous, alcoholic, hydro-alcoholic, or organic solutions thereof.

9. The synergistic composition as claimed in claim 1, where in the composition is formulated into a dosage form selected from the group consisting of a dry powder form, a liquid form, a beverage, a water dispersible formulation, a food product, a dietary supplement, a tablet, a capsule, a soft chewable, and a gummy bear.

10. The synergistic composition as claimed in claim 1, wherein the composition is formulated into a dosage form comprising a food product selected from the group consisting of a solid food, a water dispersible beverage, a semisolid food, a beverage, a lactic acid bacteria beverage, a drop, a candy, a chewing gum, a gummy candy, yoghurt, ice cream, pudding, a soft adzuki bean jelly, jelly, a cookie, a tea, a soft drink, a juice, a milk, coffee, cereal, and a snack bar.

11. The synergistic composition as claimed in claim 1, wherein the pharmaceutically or nutraceutically or dietetically acceptable excipients, carriers and diluents are selected from the group consisting of glucose, dextrose, fructose, galactose, sucrose, maltose, lactose, lactulose, trehalose, cellobiose, chitobiose, starch, sodium starch glycolate, pre gelatinized starch, soluble starch, yellow dextrin, white dextrin, maltodextrin, alginates, sorbitol, mannitol, inositol, xylitol, isomalt, microcrystalline cellulose, hydroxy propyl methyl cellulose, hydroxy ethyl cellulose, silicates, talc, colloidal silicon dioxide, calcium stearate, magnesium stearate, zinc stearate, citric acid, tartaric acid, malic acid, succinic acid, lactic acid, L-ascorbic acid, fatty acid esters, esters of poly sorbate, *acacia*, carrageenan, guar gum, xanthan gum, nicotinamide, calcium pantothenate, amino acids, casein, gelatin, pectin, agar, sodium chloride, calcium chloride, sodium hydroxide, potassium chloride, potassium hydroxide, dicalcium phosphate, zinc sulphate, zinc chloride, natural pigments, flavors, Class I & Class II preservatives, mixtures thereof, and solutions thereof.

12. A synergistic herbal composition effective for at least one of inhibiting adipogenesis, increasing adipolysis, and increasing FGF21 activity in a patient in need thereof, the synergistic composition comprising a combination of:
a first ingredient, wherein the first ingredient is an extract of a *Theobroma cacao* seed, wherein the first ingredient comprises 0.1% to 20% by weight of theobromine; and
a second ingredient, wherein the second ingredient is an extract of a *Citrus aurantifolia* fruit peel, wherein the second ingredient comprises 0.1% to 10% by weight of limonin;
wherein the first ingredient and the second ingredient are present in the synergistic herbal composition in a ratio ranging from 1:3 to 3:1 by weight.

13. The synergistic composition as claimed in claim 12, wherein the first ingredient and the second ingredient are produced by extraction using at least one solvent selected from the group consisting of C1-C5 alcohols, ketones chlorinated solvents, water, C1-C7 hydrocarbons, esters, and mixtures thereof.

14. The synergistic composition as claimed in claim 12, wherein the first ingredient and the second ingredient are produced by extraction with a solvent selected from the group consisting of ethanol, methanol, n-propanol, isopropyl alcohol, acetone, methyl isobutyl ketone, methylene dichloride, chloroform, water, hexane, ethyl acetate, and mixtures thereof.

15. The synergistic herbal composition as claimed in claim 12, wherein the synergistic herbal composition consists of the first ingredient and the second ingredient.

* * * * *